(12) United States Patent
Lalleman et al.

(10) Patent No.: US 8,790,623 B2
(45) Date of Patent: *Jul. 29, 2014

(54) COMPOSITION FOR TREATING KERATIN FIBERS, COMPRISING AT LEAST ONE AROMATIC ALCOHOL, AT LEAST ONE AROMATIC CARBOXYLIC ACID, AND AT LEAST ONE PROTECTING AGENT

(75) Inventors: Boris Lalleman, Paris (FR); Franck Giroud, Clichy (FR)

(73) Assignee: Il'Oreal, Paris (FR)

( * ) Notice: Subject to any disclaimer, the term of this patent is extended or adjusted under 35 U.S.C. 154(b) by 897 days.

This patent is subject to a terminal disclaimer.

(21) Appl. No.: 11/333,292

(22) Filed: Jan. 18, 2006

(65) Prior Publication Data

US 2006/0182697 A1 Aug. 17, 2006

Related U.S. Application Data

(60) Provisional application No. 60/651,515, filed on Feb. 10, 2005.

(30) Foreign Application Priority Data

Jan. 18, 2005 (FR) ...................... 05 50142

(51) Int. Cl.
*A61K 8/18* (2006.01)
*A61Q 5/00* (2006.01)
*A61Q 5/06* (2006.01)
*A61Q 5/10* (2006.01)
*A61Q 17/04* (2006.01)

(52) U.S. Cl.
USPC .......... 424/59; 424/70.1; 424/70.6; 424/70.9; 424/DIG. 1; 514/844; 514/880; 514/881

(58) Field of Classification Search
USPC ......................................................... 424/59
See application file for complete search history.

(56) References Cited

U.S. PATENT DOCUMENTS

| | | | |
|---|---|---|---|
| 2,261,002 A | 10/1941 | Ritter | |
| 2,271,378 A | 1/1942 | Searle | |
| 2,273,780 A | 2/1942 | Dittmar | |
| 2,294,613 A | 9/1942 | Winkelmann | |
| 2,375,853 A | 5/1945 | Kirby et al. | |
| 2,388,614 A | 11/1945 | Kirby et al. | |
| 2,454,547 A | 11/1948 | Bock et al. | |
| 2,463,264 A | 3/1949 | Graenecher et al. | |
| 2,528,378 A | 10/1950 | Mannheimer | |
| 2,781,354 A | 2/1957 | Mannheimer | |
| 2,961,347 A | 11/1960 | Floyd | |
| 3,206,462 A | 9/1965 | McCarty | |
| 3,227,615 A | 1/1966 | Korden | |
| 3,632,559 A | 1/1972 | Matter et al. | |
| 3,697,644 A * | 10/1972 | Laiderman | .................. 424/70.1 |
| 3,874,870 A | 4/1975 | Green et al. | |
| 3,910,862 A | 10/1975 | Barabas et al. | |
| 3,912,808 A | 10/1975 | Sokol | |
| 3,917,817 A | 11/1975 | Vanlerberghe et al. | |
| 3,929,990 A | 12/1975 | Green et al. | |
| 3,966,904 A | 6/1976 | Green et al. | |
| 3,986,825 A | 10/1976 | Sokol | |
| 4,001,432 A | 1/1977 | Green et al. | |
| 4,003,699 A | 1/1977 | Rose et al. | |
| 4,005,193 A | 1/1977 | Green et al. | |
| 4,013,787 A | 3/1977 | Varlerberghe et al. | |
| 4,025,617 A | 5/1977 | Green et al. | |
| 4,025,627 A | 5/1977 | Green et al. | |
| 4,025,653 A | 5/1977 | Green et al. | |
| 4,026,945 A | 5/1977 | Green et al. | |
| 4,027,008 A | 5/1977 | Sokol | |
| 4,027,020 A | 5/1977 | Green et al. | |
| 4,075,136 A | 2/1978 | Schaper | |
| 4,137,180 A | 1/1979 | Naik et al. | |
| 4,165,367 A | 8/1979 | Chakrabarti | |
| 4,166,894 A | 9/1979 | Schaper | |
| 4,172,887 A | 10/1979 | Vanlerberghe et al. | |
| RE30,199 E | 1/1980 | Rose et al. | |
| 4,189,468 A | 2/1980 | Vanlerberghe et al. | |
| 4,197,865 A | 4/1980 | Jacquet et al. | |
| 4,217,914 A | 8/1980 | Jacquet et al. | |
| 4,223,009 A | 9/1980 | Chakrabarti | |

(Continued)

FOREIGN PATENT DOCUMENTS

DE 23 59 399 6/1975
DE 38 43 892 6/1990

(Continued)

OTHER PUBLICATIONS

Tsujiura et al. (from IDS May 18, 2006) JP 05-043437, Translation.*

(Continued)

*Primary Examiner* — Alton Pryor
(74) *Attorney, Agent, or Firm* — The Marbury Law Group, PLLC.

(57) ABSTRACT

Disclosed herein is a cosmetic composition comprising, in a physiologically acceptable aqueous medium: at least one agent for protecting keratin fibers; at least one aromatic alcohol; and at least one aromatic carboxylic acid or a salt thereof. Also disclosed herein is a method for protecting keratin fibers against the action of atmospheric agents comprising applying the composition above to fibers. Further disclosed herein is a method for the post-treatment of an oxidation dyeing or of a direct dyeing operation on keratin fibers comprising applying the composition described above to the fibers.

44 Claims, No Drawings

(56) References Cited

U.S. PATENT DOCUMENTS

| | | | |
|---|---|---|---|
| 4,240,450 | A | 12/1980 | Grollier et al. |
| 4,277,581 | A | 7/1981 | Vanlerberghe et al. |
| 4,348,202 | A | 9/1982 | Grollier et al. |
| 4,349,532 | A | 9/1982 | Vanlerberghe et al. |
| 4,381,919 | A | 5/1983 | Jacquet et al. |
| 4,422,853 | A | 12/1983 | Jacquet et al. |
| 4,445,521 | A | 5/1984 | Grollier et al. |
| 4,579,732 | A | 4/1986 | Grollier et al. |
| 4,591,610 | A | 5/1986 | Grollier |
| 4,592,908 | A | 6/1986 | Wajaroff et al. |
| 4,608,250 | A | 8/1986 | Jacquet et al. |
| 4,693,935 | A | 9/1987 | Mazurek |
| 4,719,099 | A | 1/1988 | Grollier et al. |
| 4,728,571 | A | 3/1988 | Clemens et al. |
| 4,761,273 | A | 8/1988 | Grollier et al. |
| 4,777,040 | A | 10/1988 | Grollier et al. |
| 4,803,221 | A | 2/1989 | Bair |
| 4,839,166 | A | 6/1989 | Grollier et al. |
| 4,874,554 | A | 10/1989 | Lange et al. |
| 4,948,579 | A | 8/1990 | Jacquet et al. |
| 4,957,732 | A | 9/1990 | Grollier et al. |
| 4,970,066 | A | 11/1990 | Grollier et al. |
| 4,972,037 | A | 11/1990 | Garbe et al. |
| 4,996,059 | A | 2/1991 | Grollier et al. |
| 5,009,880 | A | 4/1991 | Grollier et al. |
| 5,061,289 | A | 10/1991 | Clausen et al. |
| 5,089,252 | A | 2/1992 | Grollier et al. |
| 5,139,037 | A | 8/1992 | Grollier et al. |
| 5,196,189 | A | 3/1993 | Jacquet et al. |
| 5,227,153 | A | 7/1993 | Grollier et al. |
| 5,240,695 | A | 8/1993 | Dubief et al. |
| 5,292,529 | A * | 3/1994 | Gregory et al. ............ 424/59 |
| 5,380,340 | A | 1/1995 | Neunhoeffer et al. |
| 5,534,267 | A | 7/1996 | Neunhoeffer et al. |
| 5,585,091 | A | 12/1996 | Pelzer et al. |
| 5,616,746 | A | 4/1997 | Mahieu et al. |
| 5,618,523 | A | 4/1997 | Zysman et al. |
| 5,663,366 | A | 9/1997 | Neunhoeffer et al. |
| 5,670,160 | A | 9/1997 | Eggensperger et al. |
| 5,695,748 | A | 12/1997 | Francis |
| 5,708,151 | A | 1/1998 | Möckli |
| 5,756,076 | A * | 5/1998 | Cervantes et al. ............ 424/70.1 |
| 5,766,576 | A | 6/1998 | Löwe et al. |
| 5,773,611 | A | 6/1998 | Zysman et al. |
| 5,792,221 | A | 8/1998 | Lagrange et al. |
| 5,833,997 | A | 11/1998 | Mahieu et al. |
| 5,958,392 | A | 9/1999 | Grollier et al. |
| 5,989,529 | A | 11/1999 | Kaplan |
| 6,001,376 | A | 12/1999 | Mahieu et al. |
| 6,093,385 | A | 7/2000 | Habeck et al. |
| 6,099,592 | A | 8/2000 | Vidal et al. |
| 6,159,455 | A | 12/2000 | Habeck et al. |
| 6,191,301 | B1 | 2/2001 | Habeck et al. |
| 6,210,691 | B1 | 4/2001 | Mahieu et al. |
| 6,211,125 | B1 | 4/2001 | Crudele et al. |
| 6,238,649 | B1 | 5/2001 | Habeck et al. |
| 6,284,003 | B1 | 9/2001 | Rose et al. |
| 6,338,741 | B1 | 1/2002 | Vidal et al. |
| 6,358,502 | B1 | 3/2002 | Tanabe et al. |
| 6,387,355 | B2 | 5/2002 | Heidenfelder et al. |
| 6,391,289 | B2 | 5/2002 | Heidenfelder et al. |
| 6,436,373 | B1 | 8/2002 | Habeck et al. |
| 6,545,174 | B2 | 4/2003 | Habeck et al. |
| 6,645,258 | B2 | 11/2003 | Vidal et al. |
| 6,740,317 | B1 | 5/2004 | Cho et al. |
| 6,824,764 | B2 | 11/2004 | Devin-Baudoin et al. |
| 6,824,765 | B2 | 11/2004 | Gawtrey et al. |
| 2002/0058017 | A1* | 5/2002 | Tajima et al. ............ 424/70.1 |
| 2002/0139384 | A1 | 10/2002 | Kamis et al. |
| 2002/0165283 | A1* | 11/2002 | Lutz ............ 514/642 |
| 2002/0182238 | A1 | 12/2002 | Creton |
| 2004/0048836 | A1 | 3/2004 | Wilmott |
| 2005/0013782 | A1 | 1/2005 | Goppel et al. |
| 2005/0013786 | A1 | 1/2005 | Sabbagh et al. |
| 2005/0196369 | A1* | 9/2005 | Ueyama et al. ............ 424/70.2 |

FOREIGN PATENT DOCUMENTS

| | | | |
|---|---|---|---|
| DE | 40 26 756 | | 2/1992 |
| DE | 41 33 957 | | 4/1993 |
| DE | 44 11 856 | | 10/1994 |
| DE | 44 02 929 | | 6/1995 |
| DE | 44 20 736 | | 8/1995 |
| DE | 44 24 530 | | 1/1996 |
| DE | 44 24 533 | | 1/1996 |
| DE | 195 43 988 | | 5/1997 |
| DE | 197 46 654 | | 2/1999 |
| DE | 197 55 649 | | 6/1999 |
| DE | 100 51 773 | | 4/2002 |
| DE | 101 62 844 | | 7/2003 |
| DE | 102 19 433 | A1 | 11/2003 |
| DE | 203 15 174 | | 12/2003 |
| EP | 0 080 976 | | 6/1983 |
| EP | 0 122 324 | | 10/1984 |
| EP | 0 186 507 | | 7/1986 |
| EP | 0 227 994 | | 7/1987 |
| EP | 275719 | A2 * | 7/1988 |
| EP | 0 329 032 | | 8/1989 |
| EP | 0 337 354 | | 10/1989 |
| EP | 0 342 834 | | 11/1989 |
| EP | 0 412 704 | | 2/1991 |
| EP | 0 412 707 | | 2/1991 |
| EP | 0 437 006 | A1 | 7/1991 |
| EP | 0 486 135 | | 5/1992 |
| EP | 0 521 651 | | 1/1993 |
| EP | 0 582 152 | | 2/1994 |
| EP | 0 640 105 | | 3/1995 |
| EP | 0 646 572 | | 4/1995 |
| EP | 0 669 323 | | 8/1995 |
| EP | 0 714 954 | | 6/1996 |
| EP | 0 770 375 | | 5/1997 |
| EP | 0 832 642 | | 4/1998 |
| EP | 0 967 200 | | 12/1999 |
| EP | 0 981 318 | A1 | 3/2000 |
| EP | 1 008 586 | | 6/2000 |
| EP | 1 027 883 | | 8/2000 |
| EP | 1 118 319 | A1 | 7/2001 |
| EP | 1 133 980 | | 9/2001 |
| EP | 1 133 981 | | 9/2001 |
| EP | 1 300 137 | | 4/2003 |
| EP | 1 468 667 | A1 | 10/2004 |
| EP | 1 568 350 | A2 | 8/2005 |
| FR | 1 583 363 | | 10/1969 |
| FR | 2 077 143 | | 10/1971 |
| FR | 2 080 759 | | 11/1971 |
| FR | 2 162 025 | | 7/1973 |
| FR | 2 190 406 | | 2/1974 |
| FR | 2 252 840 | | 6/1975 |
| FR | 2 270 846 | | 12/1975 |
| FR | 2 280 361 | | 2/1976 |
| FR | 2 316 271 | | 1/1977 |
| FR | 2 320 330 | | 3/1977 |
| FR | 2 336 434 | | 7/1977 |
| FR | 2 368 508 | | 5/1978 |
| FR | 2 383 660 | | 10/1978 |
| FR | 2 393 573 | | 1/1979 |
| FR | 2 413 907 | | 8/1979 |
| FR | 2 470 596 | | 6/1981 |
| FR | 2 505 348 | | 11/1982 |
| FR | 2 519 863 | | 7/1983 |
| FR | 2 542 997 | | 9/1984 |
| FR | 2 589 476 | | 5/1987 |
| FR | 2 598 611 | | 11/1987 |
| FR | 2 627 085 | | 8/1989 |
| FR | 2 673 179 | | 8/1992 |
| FR | 2 673 839 | | 9/1992 |
| FR | 2 692 572 | | 12/1993 |
| FR | 2 733 749 | | 11/1996 |
| FR | 2 795 319 | A1 | 12/2000 |
| FR | 2831810 | | 5/2003 |
| FR | 2831812 | | 5/2003 |
| GB | 1 026 978 | | 4/1966 |
| GB | 1 096 943 | | 12/1967 |
| GB | 1 153 196 | | 5/1969 |
| GB | 1 546 809 | | 5/1979 |

(56) References Cited

FOREIGN PATENT DOCUMENTS

| | | |
|---|---|---|
| ID | 198 55 649 | 6/2000 |
| JP | 2-19576 | 1/1990 |
| JP | 5-43437 | 2/1993 |
| JP | 5-043437 | 2/1993 |
| JP | 5-163124 | 6/1993 |
| JP | 2000-247841 | 9/2000 |
| JP | 2001-213741 A | 8/2001 |
| JP | 2003-513897 | 4/2003 |
| JP | 2003-286153 | 10/2003 |
| WO | WO 93/04665 | 3/1993 |
| WO | WO 93/11103 | 6/1993 |
| WO | WO 93/23009 | 11/1993 |
| WO | WO 94/07844 | 4/1994 |
| WO | WO 94/08969 | 4/1994 |
| WO | WO 94/08970 | 4/1994 |
| WO | WO 94/10131 | 5/1994 |
| WO | WO 94/24097 | 10/1994 |
| WO | WO 95/00578 | 1/1995 |
| WO | WO 95/01772 | 1/1995 |
| WO | WO 95/15144 | 6/1995 |
| WO | WO 95/16655 | 6/1995 |
| WO | WO 95/23807 | 9/1995 |
| WO | WO 96/15765 | 5/1996 |
| WO | WO 98/51265 A1 | 11/1998 |
| WO | WO 01/34103 | 5/2001 |
| WO | WO 01/70189 | 9/2001 |
| WO | WO 2004/098550 A1 | 11/2004 |

OTHER PUBLICATIONS

Pande et al. "Hair photoprotection dyes" J. Cosmet. Sci., Nov./Dec. 2001, 52, pp. 377-389.*
Electromagnetic Spectrum accessed at http://hyperphysics.phys-astr.gsu.edu/hgase/ems3.html accessed on Jun. 13, 2013.*
Ghasemi et al. "Simultaneous Spectrophotomeric Determination of Benzyl Alcohol and Diclofenac in Pharmaceutical Formulations by Chemometrics Methods," Journal of the Chinese Chemical Society 2005, 52, pp. 1049-1054.*
"Simultaneous Analysis of Phenoxyethanol and Parabens," accessed on Jun. 13, 2013 at http://www,hitachi-hitec.com/global/science/lc/img/chromaster_data12/cm_data12.pdf that phenoxyethanol.*
Office Action dated Jun. 24, 2010 for U.S. Appl. No. 11/476,076.
English language abstract for JP 5-043437, 1993.
European Search Report for EP 05 29 2642, dated Apr. 26, 2005.
English language machine translation of DE 102 19 433 A1., 2003.
Copending U.S. Appl. No. 11/476,076, filed Jun. 28, 2006, published as US2007/0056121 A1.
English language Abstract of EP 1 468 667, 2004.
English language Abstract of JP 2001-213741, 2001.
Anonymous, "The Use of UV Filters in Cosmetic and Pharmaceutical Sunscreen Formulations," IP Com Journal, 2002, pp. 1-35, New York, USA.
European Search Report corresponding to EP 06 11 5282, dated Oct. 19, 2006.
French Search Report corresponding to FR 05/51794, dated Mar. 9, 2006.
Umbach: Entwicklung, Herstellung and Anwendung Kosmetischer Mitell: 2. Auflage (1995), Cited in European Opposition Proceedings for Related Patent No. EP 1688127.
English-language Abstract of FR 2795319 A1, 2000.
European Opposition Proceedings, up to May 2, 2010, for Related Patent No. EP 1688127.
Dorgan, P.D., "Waxes in Cosmetics," *Drug and Cosmetic Industry*, 133(6): 30-33 (1983).
Todd & Byers, "Volatile silicone fluids for cosmetics," *Cosmetics & Toiletries* 91: 27-32 (1976).
Porter, M.R., *Handbook of Surfactants*, Blackie: Glasgow & London, pp. 116-178 (1991).
French Search Report for FR 05/50142, mailed Sep. 1, 2005 (corresponding to the present application).
English language Derwent abstract for DE 100 51 773.
English language Derwent abstract for DE 203 15 174 U1.
English language Derwent abstract for DE 44 02 929.
English language Derwent abstract for DE 44 20 736.
English language Derwent abstract for DE 44 11 856.
English language Derwent abstract for DE 44 24 530.
English language Derwent abstract for DE 44 24 533.
English language Derwent abstract for EP 0 080 976.
English language Derwent abstract for EP 0 770 375.
English language Derwent abstract for FR 2 589 476.
English language Derwent abstract for FR 2 673 839.
English language Derwent abstract for JP 2-19576.
English language Derwent abstract for JP 5-43437.
English language Derwent abstract for JP 5-163124.
English language Derwent abstract for WO 93/04665.
English language Derwent abstract for WO 95/23807.

* cited by examiner

COMPOSITION FOR TREATING KERATIN FIBERS, COMPRISING AT LEAST ONE AROMATIC ALCOHOL, AT LEAST ONE AROMATIC CARBOXYLIC ACID, AND AT LEAST ONE PROTECTING AGENT

This application claims benefit of U.S. Provisional Application No. 60/651,515, filed Feb. 10, 2005, the contents of which are incorporated herein by reference. This application also claims benefit of priority under 35 U.S.C. §119 to French Patent Application No. 05 50142, filed Jan. 18, 2005, the contents of which are also incorporated herein by reference.

Disclosed herein is a composition for treating keratin fibers, such as the hair, comprising, in a physiologically acceptable, for example, a cosmetically acceptable aqueous, medium, at least one aromatic alcohol, at least one aromatic acid, and at least one protecting agent. Also disclosed herein is a method for treating keratin fibers, for example, the post-treatment of a direct or oxidation dyeing operation, comprising applying the composition of the present disclosure to the keratin fibers.

It is well known that the hair is sensitized and/or embrittled to varying degrees by the action of atmospheric agents, for example, light. Many publications disclose that natural light destroys certain amino acids of the hair. These attacking factors may impair the hair fiber and reduce its mechanical properties, for instance the tensile strength, the breaking load and the elasticity, and/or its resistance to swelling in an aqueous medium. The hair is then dull, coarse, and/or brittle.

It is also known that light especially has a tendency to attack the natural color of the hair, and also the artificial color of dyed hair. The color of the hair gradually may fade or turn to relatively unattractive or undesirable shades.

The effect of light may be even more visible on hair dyed by artificial coloration, for example, oxidation dyeing and direct dyeing. In this case, exposure to light may lead to degradation of the dyes present both in the hair and on its surface. This results in substantial fading and/or changing of the color of the hair.

Substances for protecting the hair against the degradation caused by atmospheric attacking factors, such as light, have been sought for many years in the cosmetics industry. Products that protect the integrity of keratin fibers, i.e., their composition, their surface condition, their natural or artificial color and their intrinsic mechanical properties (the tensile strength, breaking load and elasticity, and/or their resistance to swelling in an aqueous medium) would be desirable.

To combat these types of degradation of hair keratin, it has been proposed to use protecting agents such as organic UV-screening agents, antioxidants, chelating agents, and/or free-radical scavengers.

Certain substances capable of screening out light radiation, for instance 2-hydroxy-4-methoxybenzophenone-5-sulfonic acid and salts thereof (discussed, for example, in French Patent Application No. 2 627 085), 4-(2-oxo-3-bornylidenemethyl)-benzenesulfonic acid or salts thereof (discussed, for example, in European Patent Application No. 0 329 032), and lactoferrin (discussed, for example, in French Patent Application No. 2 673 839) have thus been proposed.

Japanese Patent Application No. 05-043 437 discloses dye compositions containing 2-hydroxy-4-methoxybenzophenone-5-sulfonic acid and salts thereof, an aromatic alcohol, and an acidic direct dye.

However, the current cosmetic compositions containing protecting agents are not always entirely satisfactory, in particular on hair dyed with blue oxidation dyes, for instance those obtained with couplings comprising meta-phenylenediamines.

The present inventors have now discovered, surprisingly, that aqueous compositions comprising a combination of an aromatic alcohol, an aromatic carboxylic acid, and a protecting agent may give the hair better protection against the harmful effects of light. An improvement in the light-fastness of the coloration of hair dyed by direct dyeing or oxidation dyeing may be observed.

Thus, disclosed herein are novel cosmetic compositions comprising, in a physiologically acceptable aqueous medium:

a) at least one agent for protecting keratin fibers, chosen from organic UV-screening agents, free-radical scavengers, and antioxidants, present in the composition in an amount ranging from 0.2% to 20% by weight relative to the total weight of the composition;

b) at least one aromatic alcohol, present in the composition in an amount of greater than 1% by weight relative to the total weight of the composition; and c) at least one aromatic carboxylic acid or a salt thereof.

Also disclosed herein is a method for treating keratin fibers, such as the hair, and/or protecting keratin fibers against atmospheric agents, comprising applying to the keratin materials a cosmetic composition as defined above, and then optionally rinsing with water.

The present disclosure also relates to the use of a composition as defined above in the preparation of a cosmetic formulation for protecting keratin fibers against the action of atmospheric agents.

Further disclosed herein is a method for the post-treatment of an oxidation dyeing or a direct dyeing operation on keratin fibers, such as the hair, comprising applying a composition as defined above to the keratin fibers.

Still further disclosed herein is a dyeing process comprising applying to human keratin fibers, such as the hair, a direct or oxidation dye composition (A) for a time that is sufficient to develop the color, and, after optionally rinsing and optionally drying, by subsequently applying a composition (B) comprising a composition as defined above.

Other characteristics, aspects, subjects, and advantages of the present disclosure will emerge even more clearly on reading the description and the examples which follow. All of the meanings and definitions of the compounds presented herein are valid for all of the subjects of the present disclosure.

Compositions

Physiologically Acceptable Medium

The physiologically acceptable, and in at least one embodiment, cosmetically acceptable, medium may comprise water, at least one aromatic alcohol and at least one aromatic carboxylic acid. It may comprise at least one cosmetically acceptable organic solvent other than aromatic alcohols and aromatic carboxylic acids. Examples of cosmetically acceptable organic solvents include, but are not limited to, $C_1$-$C_4$ lower alcohols, for instance, ethanol, isopropanol, tert-butanol, and n-butanol; polyols, for instance, propylene glycol, glycerol, diethylene glycol, and polyol ethers. In at least one embodiment, the cosmetically acceptable organic solvent may be ethanol.

Agent for Protecting Keratin Fibers

The agent for protecting keratin fibers may be any active agent that is useful for preventing or limiting the degradation of keratin fibers, such as the hair, caused by atmospheric attacking factors, for example, light.

The agent for protecting keratin fibers may be chosen from organic UV-screening agents, free-radical scavengers, and antioxidants.

As used herein, the term "free-radical scavenger" means any compound capable of trapping free radicals.

The organic UV-screening agents (systems for screening out UV radiation) may be chosen from water-soluble or lipo-soluble, silicone or non-silicone screening agents.

The organic screening agents may be chosen, for example, from dibenzoylmethane derivatives; anthranilates; cinnamic derivatives; salicylic derivatives; camphor derivatives; benzophenone derivatives; β,β-diphenylacrylate derivatives; triazine derivatives; benzotriazole derivatives; benzalmalonate derivatives; benzimidazole derivatives; imidazolines; bis-benzazolyl derivatives, described, for example, in European Patent No. 0 669 323 and U.S. Pat. No. 2,463,264; p-aminobenzoic acid (PABA) derivatives; benzoxazole derivatives, described, for example, in European Patent Application Nos. 0 832 642, 1 027 883, and 1 300 137 and German Patent Application No. 101 62 844; screening polymers and screening silicones such as those described in International Patent Application Publication No. WO 93/04665; dimers derived from (α-alkyl-styrene, such as those described in patent application DE 198 55 649; 4,4-diarylbutadienes such as those described in European Patent Application Nos. 0 967 200, 1 008 586, 1 133 980, and 1 133 981, and German Patent Application Nos. 197 46 654 and 197 55 649, and mixtures thereof.

Examples of organic UV-screening agents include, but are not limited to, the following compounds, as denoted by their INCI names:

para-Aminobenzoic Acid Derivatives:
PABA,
Ethyl PABA,
Ethyl dihydroxypropyl PABA,
Ethylhexyl dimethyl PABA sold, for example, under the name "Escalol 507" by ISP,
Glyceryl PABA, and
PEG-25 PABA, sold, for example, under the name "Uvinul P25" by BASF.

Cinnamic Derivatives:
Ethylhexyl methoxycinnamate sold, for example, under the trade name "Parsol MCX" by Hoffmann LaRoche,
Isopropyl methoxycinnamate,
Isoamyl methoxycinnamate sold, for example, under the trade name "Neo Heliopan E 1000" by Haarmann and Reimer,
Cinoxate,
DEA methoxycinnamate,
Diisopropyl methylcinnamate, and
Glyceryl ethylhexanoate dimethoxycinnamate.

Dibenzoylmethane Derivatives:
Butylmethoxydibenzoylmethane sold, for example, under the trade name "Parsol 1789" by Hoffmann LaRoche, and
Isopropyldibenzoylmethane sold, for example, under the trade name "Eusolex 8020" by Merck.

Salicylic Derivatives:
Homosalate sold, for example, under the name "Eusolex HMS" by Rona/EM Industries,
Ethylhexyl salicylate sold, for example, under the name "Neo Heliopan OS" by Haarmann and Reimer,
Dipropylene glycol salicylate sold, for example, under the name "Dipsal" by Scher, and TEA salicylate sold, for example, under the name "Neo Heliopan TS" by Haarmann and Reimer.

β,β-Diphenylacrylate Derivatives:
Octocrylene sold, for example, under the trade name "Uvinul N539" by BASF, and
Etocrylene sold, for example, under the trade name "Uvinul N35" by BASF.

Benzophenone Derivatives:
Benzophenone-1 sold, for example, under the trade name "Uvinul 400" by BASF,
Benzophenone-2 sold, for example, under the trade name "Uvinul D50" by BASF,
Benzophenone-3 or Oxybenzone sold, for example, under the trade name "Uvinul M40" by BASF,
Benzophenone-4 sold, for example, under the trade name "Uvinul MS40" by BASF,
Benzophenone-5,
Benzophenone-6 sold, for example, under the trade name "Helisorb 11" by Norquay,
Benzophenone-8 sold, for example, under the trade name "Spectra-Sorb UV-24" by American Cyanamid,
Benzophenone-9 sold, for example, under the trade name "Uvinul DS-49" by BASF,
Benzophenone-12, and
n-hexyl 2-(4-diethylamino-2-hydroxybenzoyl)benzoate.

Benzylidenecamphor Derivatives:
3-Benzylidenecamphor manufactured, for example, under the name "Mexoryl SD" by Chimex,
4-Methylbenzylidenecamphor sold, for example, under the name "Eusolex 6300" by Merck,
Benzylidenecamphorsulfonic acid manufactured, for example, under the name "Mexoryl SL" by Chimex,
Camphor benzalkonium methosulfate manufactured, for example, under the name "Mexoryl SO" by Chimex,
Terephthalylidenedicamphorsulfonic acid manufactured, for example, under the name "Mexoryl SX" by Chimex, and
Polyacrylamidomethylbenzylidenecamphor manufactured, for example, under the name "Mexoryl SW" by Chimex.

Phenylbenzimidazole Derivatives:
Phenylbenzimidazolesulfonic acid sold, for example, under the trade name "Eusolex 232" by Merck, and
Disodium phenyl dibenzimidazole tetrasulfonate sold, for example, under the trade name "Neo Heliopan AP" by Haarmann and Reimer.

Phenylbenzotriazole derivatives:
Drometrizole trisiloxane sold, for example, under the name "Silatrizole" by Rhodia Chimie, and
Methylenebis(benzotriazolyl)tetramethylbutylphenol sold, for example, in solid form under the trade name "MIXXIM BB/100" by Fairmount Chemical, or in micronized form as an aqueous dispersion, for example, under the trade name "Tinosorb M" by Ciba Specialty Chemicals.

Triazine Derivatives:
Bis-Ethylhexyloxyphenol Methoxyphenyl Triazine sold, for example, under the trade name "Tinosorb S" by Ciba Geigy,
Ethylhexyltriazone sold, for example, under the trade name "Uvinul T150" by BASF,
Diethylhexylbutamidotriazone sold, for example, under the trade name "Uvasorb HEB" by Sigma 3V, and
2,4,6-tris(diisobutyl 4'-aminobenzalmalonate)-s-triazine.

Anthranilic Derivatives:
Menthyl anthranilate sold, for example, under the trade name "Neo Heliopan MA" by Haarmann and Reimer.

Imidazoline Derivatives:
Ethylhexyldimethoxybenzylidenedioxoimidazoline propionate.

Benzalmalonate Derivatives:
Polyorganosiloxane containing benzalmalonate functions, for instance Polysilicone-15, sold, for example, under the trade name "Parsol SLX" by Hoffmann LaRoche
4,4-Diarylbutadiene Derivatives:
1,1-Dicarboxy(2,2'-dimethylpropyl)-4,4-diphenylbutadiene
Benzoxazole Derivatives:
2,4-bis[5-(1-dimethylpropyl)benzoxazol-2-yl(4-phenyl)imino]-6-(2-ethylhexyl)imino-1,3,5-triazine sold, for example, under the name Uvasorb K2A by Sigma 3V, and mixtures thereof.

Non-limiting examples of liposoluble (or lipophilic) organic UV-screening agents include:
ethylhexyl methoxycinnamate,
butylmethoxydibenzoylmethane,
Homosalate,
ethylhexyl salicylate,
Octocrylene,
Benzophenone-3,
n-hexyl 2-(4-diethylamino-2-hydroxybenzoyl)benzoate,
4-methylbenzylidenecamphor,
ethylhexyl triazone,
bis-ethylhexyloxyphenol methoxyphenyl triazine,
diethylhexyl butamido triazone,
drometrizole trisiloxane,
Polysilicone-15,
1,1-dicarboxy(2,2'-dimethylpropyl)-4,4-diphenylbutadiene, and
2,4-bis[5-1(dimethylpropyl)benzoxazol-2-yl(4-phenyl)imino]-6-(2-ethylhexyl)imino-1,3,5-triazine.

Suitable water-soluble (or hydrophilic) organic UV-screening agents may be chosen, for example, from:
PABA,
PEG-25 PABA,
benzylidenecamphorsulfonic acid,
camphorbenzalkonium methosulfate,
terephthalylidenedicamphorsulfonic acid,
phenylbenzimidazolesulfonic acid,
Benzophenone-4, and
Benzophenone-5.

Free-radical scavengers that may be used in the composition according to the present disclosure may comprise, besides certain antipollution agents mentioned above, vitamin E and derivatives thereof such as tocopheryl acetate; bioflavonoids; coenzyme Q10 (ubiquinone); enzymes, for instance, catalase, superoxide dismutase and wheatgerm extracts containing it, lactoperoxidase, glutathione peroxidase, and quinone reductases; glutathione; benzylidenecamphor; benzylcyclanones; substituted naphthalenones; pidolates; phytanetriol; gamma-oryzanol; guanosine; lignans; and melatonin.

Examples of antioxidants include, but are not limited to, phenols such as BHA (tert-butyl-4-hydroxyanisole), BHT (2,6-di-tert-butyl-p-cresol), TBHQ (tert-butylhydroquinone), polyphenols such as proanthocyanidol oligomers and flavonoids, hindered amines known under the generic term HALS (Hindered Amine Light Stabilizer) such as tetraaminopiperidine, erythorbic acid, polyamines such as spermine, cysteine, glutathione, superoxide dismutase, and lactoferrin.

In at least one embodiment, the agents for protecting keratin fibers may be chosen from organic UV-screening agents.

According to the present disclosure, the agent(s) for protecting keratin fibers may be present in the composition in an amount ranging from 0.2% to 20% by weight relative to the total weight of the composition.

According to one embodiment of the present disclosure, protecting agents that have a log P (octanol/water partition coefficient) of less than 9, such as less than 4, may be used.

According to another embodiment of the present disclosure, protecting agents that are soluble in the aqueous medium of the composition, for example, protecting agents that are at least 0.5% soluble in water and $C_1$-$C_4$ lower alcohols such as ethanol, at 25° C., may be used. In one embodiment, water-soluble organic UV-screening agents such as Benzophenone-4 may be used.

Aromatic Alcohols

The hair compositions according to the present disclosure may comprise at least one aromatic alcohol.

As used herein, the term "aromatic alcohol" means any compound that is liquid at room temperature and atmospheric pressure, comprising at least one entity chosen from benzene and naphthalene rings and at least one alcohol function (OH) directly linked to the ring or linked to at least one substituent of the ring. In at least one embodiment, the alcohol function may be on a substituent of the benzene or naphthalene ring.

Examples of aromatic alcohols that may be used in the composition according to the present disclosure, include, but are not limited to:
benzyl alcohol,
benzoylisopropanol,
benzyl glycol,
phenoxyethanol,
dichlorobenzyl alcohol,
methylphenylbutanol,
phenoxyisopropanol,
phenylisohexanol,
phenylpropanol,
phenylethyl alcohol, and
mixtures thereof.

In at least one embodiment, the at least one aromatic alcohol may be benzyl alcohol.

According to the present disclosure, the at least one aromatic alcohol may be present in the composition in an amount of greater than 1% by weight relative to the total weight of the composition.

Aromatic Carboxylic Acids

The compositions according to the present disclosure may also comprise at least one optionally salified aromatic carboxylic acid.

As used herein, the term "aromatic carboxylic acid" means any compound comprising at least one entity chosen from benzene and naphthalene rings and at least one carboxylic acid function (COOH), in free or salified form, directly linked to the ring or linked to at least one substituent of the ring. In at least one embodiment, the acid function may be directly linked to the benzene or naphthalene ring.

Non-limiting examples of aromatic carboxylic acid salts include alkali metal (for example, sodium and potassium) and alkaline-earth metal (for example, calcium and magnesium) salts, organic amines, and ammonium salts.

Suitable aromatic carboxylic acids that may be used in the composition according to the present disclosure may be chosen, for example, from:
benzoic acid,
para-anisic acid,
caffeic acid,
chlorogenic acid,
diphenolic acid,
ferulic acid,
hippuric acid,
3-hydroxybenzoic acid,
4-hydroxybenzoic acid, hydroxycinnamic acid,
phenylthioglycolic acid,
salicylic acid,
acetylsalicylic acid,
para-, meta-, or ortho-phthalic acid,
the salified forms thereof, and
mixtures thereof.

In at least one embodiment, the at least one aromatic carboxylic acid may be benzoic acid.

According to the present disclosure, the at least one aromatic carboxylic acid and salts thereof may be present in the composition in an amount ranging from 0.001% to 30% by weight, for example, from 0.01% to 20% by weight, or from 0.1% to 10% by weight relative to the total weight of the composition.

Conditioning Agents

The compositions according to the present disclosure may also comprise at least one conditioning agent.

As used herein, the term "conditioning agent" means any agent whose function is to improve the cosmetic properties of the hair, for example, the softness, disentangling, feel, smoothness, and/or static electricity.

The conditioning agents may be in liquid, semi-solid, or solid form, for example, oils, waxes, and gums.

According to the present disclosure, the conditioning agents may be chosen from synthetic oils such as polyolefins, plant oils, fluoro oils, perfluoro oils, natural waxes, synthetic waxes, silicones, non-polysaccharide cationic polymers, ceramide compounds, cationic surfactants, fatty amines, fatty acids and derivatives thereof, and mixtures thereof.

The synthetic oils may be chosen from polyolefins, for example, poly-α-olefins, such as poly-α-olefins
of hydrogenated or non-hydrogenated polybutene type, for instance, of hydrogenated or non-hydrogenated polyisobutene type.

In at least one embodiment, the synthetic oil may be chosen from isobutylene oligomers with a molecular weight of less than 1000 and mixtures thereof with polyisobutylenes with a molecular weight of greater than 1000, for example, ranging from 1000 to 15000.

Examples of poly-α-olefins that can be used in accordance with the present disclosure include, but are not limited to, the polyisobutenes sold under the name Permethyl 99 A, 101 A, 102 A, 104 A (n=16), and 106 A (n=38) by the company Presperse Inc., and the products sold under the name Arlamol HD (n=3) by the company ICI (n denoting the degree of polymerization),
of hydrogenated or non-hydrogenated polydecene type.

Such products are sold, for example, under the names Ethylflo by the company Ethyl Corp. and Arlamol PAO by the company ICI.

The animal or plant oils may be chosen from sunflower oil, corn oil, soybean oil, avocado oil, jojoba oil, marrow oil, grapeseed oil, sesame oil, hazelnut oil, fish oils, glyceryl tricaprocaprylate, and plant or animal oils of formula $R_9COOR_{10}$, in which $R_9$ is chosen from higher fatty acid residues comprising from 7 to 29 carbon atoms and $R_{10}$ is chosen from linear or branched hydrocarbon-based chains comprising from 3 to 30 carbon atoms, such as alkyl and alkenyl, for example, purcellin oil and liquid jojoba wax.

It is also possible to use natural or synthetic essential oils, for example, eucalyptus oil, lavendin oil, lavender oil, vetiver oil, Litsea cubeba oil, lemon oil, sandalwood oil, rosemary oil, camomile oil, savory oil, nutmeg oil, cinnamon oil, hyssop oil, caraway oil, orange oil, geraniol oil, cade oil, and bergamot oil.

The waxes may be natural (for example, anirhal and plant) or synthetic substances that are solid at room temperature (20-25° C.). They may be insoluble in water, soluble in oils, and may be capable of forming a water-repellent film.

An example of the definition of waxes may be found, for example, in P.D. Dorgan, Drug and Cosmetic Industry, December 1983, pp. 30-33.

The at least one wax may be chosen in particular from carnauba wax, candelilla wax, alfalfa wax, paraffin wax, ozokerite, plant waxes such as olive tree wax, rice wax, hydrogenated jojoba wax, and the absolute waxes of flowers such as the essential wax of blackcurrant flower sold by the company Bertin (France), animal waxes such as beeswaxes, and modified beeswaxes (cerabellina). Other waxes or waxy starting materials which can be used according to the present disclosure include, for example, marine waxes such as the product sold by the company Sophim under the reference M82, and polyolefin waxes, for example, polyethylene waxes.

In at least one embodiment, the conditioning agents may be chosen from cationic polymers and silicones.

The non-saccharide cationic polymers that may be used in accordance with the present disclosure may be chosen from all those already known to improve the cosmetic properties of hair treated with detergent compositions, for example, those described in European Patent Application No. 0 337 354 and French Patent Application Nos. 2 270 846, 2 383 660, 2 598 611, 2 470 596, and 2 519 863.

As used herein, the term "non-saccharide polymers" is understood to mean polymers that do not contain a glycoside bond between monosaccharides.

As used herein, the term "cationic polymer" denotes any polymer containing cationic groups and/or groups that may be ionized into cationic groups.

In one embodiment, the cationic polymers may be chosen from those comprising units comprising primary, secondary, tertiary, and/or quaternary amine groups that either may form part of the main polymer chain or may be borne by a side substituent directly attached thereto.

The cationic polymers may have a number-average molecular mass ranging from 500 to $5 \times 10^6$, for example, from $10^3$ to $3 \times 10^6$.

Examples of cationic polymers include, but are not limited to, polymers of the polyamine, polyamino amide, and polyquaternary ammonium type, all of which are known products.

The polymers of the polyamine, polyamino amide, and polyquaternary ammonium type that may be used in accordance with the present disclosure, may be chosen, for example, from those described in French Patent Nos 2 505 348 and 2 542 997, for instance:

(1) homopolymers and copolymers derived from acrylic and methacrylic esters and amides and comprising at least one unit chosen from the units of formulas (III)-(VI):

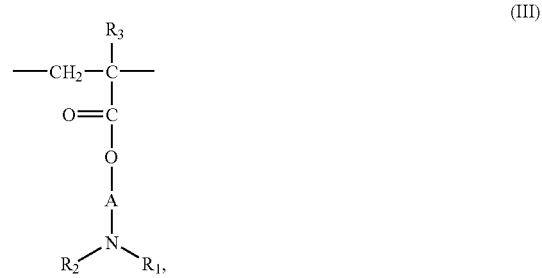

-continued

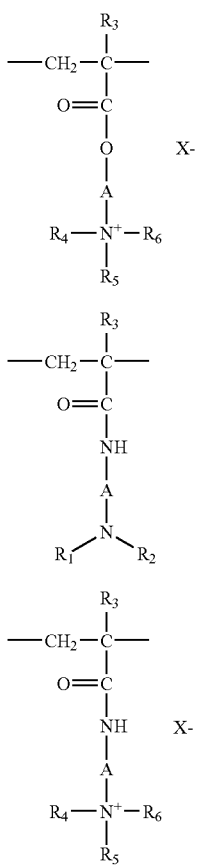

in which:

R₁ and R₂, which may be identical or different, are chosen from hydrogen and alkyl groups comprising from 1 to 6 carbon atoms, for example, methyl and ethyl;

R₃, which may be identical or different, is chosen from hydrogen and CH₃ radicals;

A, which may be identical or different, is chosen from linear or branched alkyl groups comprising from 1 to 6 carbon atoms, for example, from 2 to 3 carbon atoms, and hydroxyalkyl groups comprising from 1 to 4 carbon atoms;

R₄, R₅, and R₆, which may be identical or different, are chosen from alkyl groups comprising from 1 to 18 carbon atoms, for example, from 1 to 6 carbon atoms, and benzyl radicals; and X is an anion derived from a mineral or organic acid, for example, a methosulfate anion and a halide such as chloride and bromide.

The copolymers of family (1) may also comprise at least one unit derived from comonomers which may be chosen from acrylamides, methacrylamides, diacetone acrylamides, acrylamides and methacrylamides substituted on the nitrogen with lower ($C_1$-$C_4$) alkyls, acrylic and methacrylic acids and esters thereof, vinyllactams such as vinylpyrrolidone and vinylcaprolactam, and vinyl esters.

Non-limiting examples of copolymers of family (1) include:

copolymers of acrylamide and of dimethylaminoethyl methacrylate quaternized with an entity chosen from dimethyl sulfate and dimethyl halides, such as the product sold under the name Hercofloc by the company Hercules, copolymers of acrylamide and of methacryloyloxyethyltrimethylammonium chloride described, for example, in European Patent Application No. 0 080 976 and sold, for example, under the name Bina Quat P 100 by the company Ciba Geigy, copolymers of acrylamide and of methacryloyloxyethyltrimethylammonium methosulfate sold, for example, under the name Reten by the company Hercules, quaternized or non-quaternized vinylpyrrolidone/dialkylaminoalkyl acrylate or methacrylate copolymers, such as the products sold under the name Gafquat by the company ISP, for example, Gafquat 734 and Gafquat 755, and the products known as Copolymer 845, 958, and 937. These polymers are described, for example, in French Patent Nos. 2 077 143 and 2 393 573, dimethylaminoethyl methacrylate/vinylcaprolactam/vinylpyrrolidone terpolymers, such as the product sold under the name Gaffix VC 713 by the company ISP, vinylpyrrolidone/methacrylamidopropyldimethylamine copolymers sold, for example, under the name Styleze CC 10 by ISP, and quaternized vinylpyrrolidone/dimethylaminopropylmethacrylamide copolymers, such as the product sold under the name Gafquat HS 100 by the company ISP.

(2) Polymers comprising piperazinyl units and of divalent alkylene or hydroxyalkylene radicals comprising straight or branched chains, optionally interrupted by at least one entity chosen from oxygen, sulfur, and nitrogen atoms, and from aromatic rings and heterocyclic rings, as well as the oxidation and/or quaternization products of these polymers. Such polymers are described, for example, in French Patent Nos. 2 162 025 and 2 280 361.

(3) Water-soluble polyamino amides prepared, for example by polycondensation of an acidic compound with a polyamine; these polyamino amides may be crosslinked with an entity chosen from epihalohydrins, diepoxides, dianhydrides, unsaturated dianhydrides, bis-unsaturated derivatives, bis-halohydrins, bis-azetidiniums, bis-haloacyidiamines, bis-alkyl halides, and oligomers resulting from the reaction of a difunctional compound which is reactive with bis-halohydrins, bis-azetidiniums, bis-haloacyldiamines, bis-alkyl halides, epihalohydrins, diepoxides, and/or bis-unsaturated derivatives; the crosslinking agent being used in proportions ranging from 0.025 to 0.35 mol per amine group of the polyamino amide; these polyamino amides may be alkylated or, if they comprise one or more tertiary amine functions, they may be quaternized. Such polymers are described, for example, in French Patent Nos. 2 252 840 and 2 368 508.

(4) The polyamino amide derivatives resulting from the condensation of polyalkylene polyamines with polycarboxylic acids followed by alkylation with difunctional agents. Examples of such polymers include, but are not limited to, adipic acid/dialkylaminohydroxy-alkyldialkylenetriamine polymers in which the alkyl radical comprises from 1 to 4 carbon atoms, for example, methyl, ethyl, and propyl. Such polymers are described, for example, in French Patent No. 1 583 363.

Non-limiting examples of these derivatives are the adipic acid/dimethylamino-hydroxypropyl/diethylenetriamine polymers sold under the name Cartaretine F, F4, and F8 by the company Sandoz.

(5) The polymers obtained by reaction of a polyalkylene polyamine comprising two primary amine groups and at least one secondary amine group with a dicarboxylic acid chosen from diglycolic acid and saturated aliphatic dicarboxylic acids comprising from 3 to 8 carbon atoms. The molar ratio between the polyalkylene polyamine and the dicarboxylic acid may range from 0.8:1 to 1.4:1; the polyamino amide resulting therefrom being reacted with epichlorohydrin in a molar ratio of epichlorohydrin relative to the secondary amine group of the polyamino amide ranging from 0.5:1 to 1.8:1. Such polymers are described, for example, in U.S. Pat. Nos. 3,227,615 and 2,961,347.

Polymers of this type are sold, for example, under the name Hercosett 57 by the company Hercules Inc. and under the name PD 170 or Delsette 101 by the company Hercules in the case of the adipic acid/epoxypropyl/diethylenetriamine copolymer.

(6) Cyclopolymers of alkyldiallylamine or of dialkyldiallylammonium, such as the homopolymers or copolymers comprising, as main constituents of the chain, units chosen from those of formulas (VII) and (VIII):

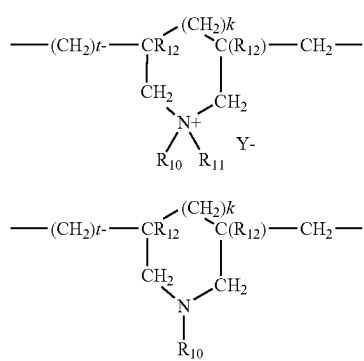

in which k and t are equal to 0 or 1, the sum k+t being equal to 1;

$R_{12}$ is chosen from hydrogen and methyl;

$R_{10}$ and $R_{11}$, which may be identical or different, are chosen from alkyl groups comprising from 1 to 6 carbon atoms, hydroxyalkyl groups in which the alkyl group comprises, for example, from 1 to 5 carbon atoms, lower ($C_1$-$C_4$) amidoalkyl groups, or alternatively, $R_{10}$ and $R_{11}$ may form, together with the nitrogen atom to which they are attached, heterocyclic groups such as piperidyl and morpholinyl; and $Y^-$ is an anion such as bromide, chloride, acetate, borate, citrate, tartrate, bisulfate, bisulfite, sulfate, and phosphate. These polymers are described, for example, in French Patent No. 2 080 759 and in its Certificate of Addition 2 190 406.

In at least one embodiment, $R_{10}$ and $R_{11}$, which may be identical or different, may be chosen from alkyl groups comprising from 1 to 4 carbon atoms.

Further examples of the polymers defined above include, but are not limited to, the dimethyldiallylammonium chloride homopolymer sold under the name Merquat 100 by the company Nalco (and its homologues of low weight-average molecular mass) and the copolymers of diallyldimethylammonium chloride and of acrylamide, sold under the name Merquat 550.

(7) The quaternary diammonium polymer comprising repeating units corresponding to formula (IX):

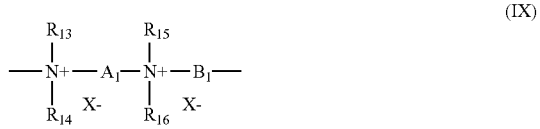

in which:

$R_{13}$, $R_{14}$, $R_{15}$, and $R_{16}$, which may be identical or different, are chosen from aliphatic, alicyclic, and arylaliphatic radicals comprising from 1 to 20 carbon atoms and lower hydroxyalkylaliphatic radicals, or alternatively, $R_{13}$, $R_{14}$, $R_{15}$, and $R_{16}$, may form together or separately, with the nitrogen atoms to which they are attached, heterocycles optionally comprising a second hetero atom other than nitrogen, or alternatively, $R_{13}$, $R_{14}$, $R_{15}$, and $R_{16}$ may be chosen from linear or branched $C_1$-$C_6$ alkyl radicals substituted with an entity chosen from nitriles, esters, acyl groups, amide groups, and —CO—O—$R_{17}$-D and —CO—NH—$R_{17}$-D groups, where $R_{17}$ is an alkylene and D is a quaternary ammonium group;

$A_1$ and $B_1$ are chosen from polymethylene groups comprising from 2 to 20 carbon atoms which may be linear or branched, saturated or unsaturated, and which may contain, linked to or intercalated in the main chain, at least one entity chosen from aromatic rings, oxygen, sulfur, sulfoxide groups, sulfone groups, disulfide groups, amino groups, alkylamino groups, hydroxyl groups, quaternary ammonium groups, ureido groups, amide groups, and ester groups, and $X^-$ is an anion derived from a mineral or organic acid;

$A_1$, $R_{13}$, and $R_{15}$ may form, together with the two nitrogen atoms to which they are attached, a piperazine ring; in addition, if $A_1$ is chosen from linear or branched, saturated or unsaturated alkylene radicals or hydroxyalkylene radicals, $B_1$ may be chosen from $(CH_2)_n$—CO-D-OC—$(CH_2)_n$— groups, wherein n is an integer ranging from about 2 to 20 and D is chosen from:

a) glycol residues of formula: —O—Z—O—, wherein Z is chosen from linear or branched hydrocarbon-based radicals and groups corresponding to one of the following formulae:

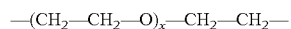

—$(CH_2-CH_2-O)_x$—$CH_2$—$CH_2$—

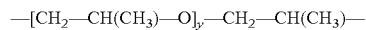

—$[CH_2-CH(CH_3)-O]_y$—$CH_2$—$CH(CH_3)$— where x and y, which may be identical or different, are integers ranging from 1 to 4, representing a defined and unique degree of polymerization or any number from 1 to 4 representing an average degree of polymerization;

b) bis-secondary diamine residues such as a piperazine derivative;

c) bis-primary diamine residues of formula: —NH—Y—NH—, wherein Y is chosen from linear or branched hydrocarbon-based radicals and the divalent radical —$CH_2$—$CH_2$—S—S—$CH_2$—$CH_2$—; and d) ureylene groups of formula: —NH—CO—NH—.

In at least one embodiment, $X^-$ may be an anion such as chloride or bromide.

These polymers generally may have a number-average molecular mass ranging from 1000 to 100 000.

Polymers of this type are described, for example, in French Patent Nos. 2 320 330, 2 270 846, 2 316 271, 2 336 434 and 2 413 907 and U.S. Pat. Nos. 2,273,780, 2,375,853, 2,388, 614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945, and 4,027,020.

Further examples of suitable polymers include those comprising repeating units corresponding to formula (a):

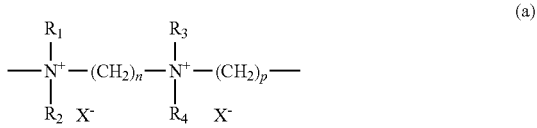

(a)

in which

R₁, R₂, R₃, and R₄, which may be identical or different, are chosen from alkyl and hydroxyalkyl radicals comprising from 1 to 4 carbon atoms, n and p are integers ranging from 2 to 20, and X⁻ is an anion derived from a mineral or organic acid.

A non-limiting example of a compound of formula (a) is the compound for which R₁, R₂, R₃, and R₄ are methyl radicals, n=3, p=6, and X=Cl, referred to as hexadimethrine chloride according to the INCI nomenclature (CTFA).

(8) polyquaternary ammonium polymers comprising units of formula (X):

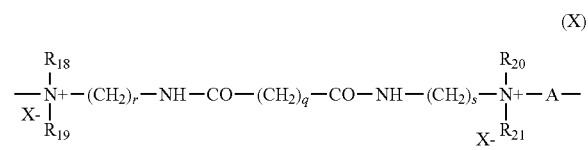

(X)

in which:

R₁₈, R₁₉, R₂₀, and R₂₁, which may be identical or different, are chosen from hydrogen and methyl, ethyl, propyl, β-hydroxyethyl, β-hydroxypropyl, and —CH₂CH₂(OCH₂CH₂)$_p$OH radicals, where p is an integer ranging from 0 to 6, with the proviso that R₁₈, R₁₉, R₂₀, and R₂₁, are not simultaneously hydrogen, r and s, which may be identical or different, are integers ranging from 1 to 6, q is an integer ranging from 0 to 34, X⁻ is an anion such as a halide, and A is chosen from dihalide radicals and —CH₂—CH₂—O—CH₂—CH₂—.

Such compounds are described, for example, in European Patent Application No. 0 122 324.

Examples of commercial products include Mirapol® A 15, Mirapol® AD1, Mirapol® AZ1, and Mirapol® 175 sold by the company Miranol.

(9) Quaternary polymers of vinylpyrrolidone and of vinylimidazole, for example, the products sold under the names Luviquat® FC 905, FC 550, and FC 370 by the company BASF.

(10) Crosslinked methacryloyloxy($C_1$-$C_4$)alkyltri($C_1$-$C_4$) alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, in particular methylenebisacrylamide. Examples of such compounds include, but are not limited to, the crosslinked acrylamide/methacryloyloxyethyltrimethylammonium chloride copolymer (20/80 by weight) in the form of a dispersion containing 50% by weight of the said copolymer in mineral oil, sold, for example, under the name Salcare® SC 92 by the company Ciba; and the crosslinked methacryloyloxy-ethyltrimethylammonium chloride homopolymer containing about 50% by weight of the homopolymer in mineral oil or in a liquid ester, sold, for example, under the names Salcare® SC 95 and Salcare® SC 96 by the company Ciba.

Other examples of cationic polymers that can be used in accordance with the present disclosure are cationic proteins and cationic protein hydrolysates, polyalkyleneimines, for example, polyethyleneimines, polymers comprising vinylpyridine or vinylpyridinium units, condensates of polyamines and of epichlorohydrin, quaternary polyureylenes, and chitin derivatives.

In at least one embodiment, the cationic polymers may be chosen from cationic cyclopolymers, for example, the dimethyldiallylammonium chloride homopolymers and copolymers sold under the names Merquat 100, Merquat 550, and Merquat S by the company Nalco, and quaternary vinylpyrrolidone and vinylimidazole polymers, and mixtures thereof.

The silicones that may be used in accordance with the present disclosure include, for example, polyorganosiloxanes that are insoluble in the composition and that may be in the form of oils, waxes, resins, or gums.

The organopolysiloxanes are defined in greater detail, for example, in Walter Noll's "Chemistry and Technology of Silicones" (1968) Academic Press. These organopolysiloxanes may be volatile or non-volatile.

When they are volatile, the silicones may be chosen from those having a boiling point ranging from 60° C. to 260° C., for example, from:

(i) cyclic silicones comprising from 3 to 7, for instance, from 4 to 5 silicon atoms. These include, for example, octamethylcyclotetrasiloxane sold, for instance, under the name Volatile Silicone 7207 by Union Carbide and Silbione 70045 V 2 by Rhodia Chimie, decamethylcyclopentasiloxane sold under the name Volatile Silicone 7158 by Union Carbide, and Silbione 70045 V 5 by Rhodia Chimie, and mixtures thereof.

Other examples of silicones include cyclocopolymers of the dimethylsiloxanes/methylalkylsiloxane type, such as Volatile Silicone FZ 3109 sold by the company Union Carbide, having the chemical structure:

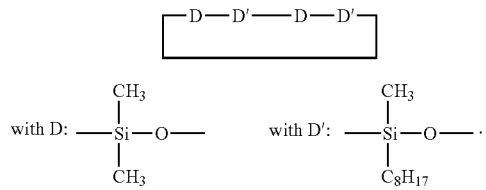

Further examples include mixtures of cyclic silicones with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;

(ii) linear volatile silicones comprising from 2 to 9 silicon atoms and having a viscosity of less than or equal to $5 \times 10^{-6}$ m²/s at 25° C. A non-limiting example of such a compound is decamethyltetrasiloxane sold, for example, under the name SH 200 by the company Toray Silicone. Silicones belonging to this category are also described in the article published in *Cosmetics and Toiletries*, Vol. 91, January 76, pp. 27-32, Todd & Byers "Volatile Silicone Fluids for Cosmetics".

In at least one embodiment, non-volatile silicones, for example, polyalkylsiloxanes, polyarylsiloxanes, polyalkylarylsiloxanes, silicone gums and resins, polyorganosiloxanes modified with organofunctional groups, and mixtures thereof, may be used in the compositions disclosed herein.

These silicones may be chosen from polyalkylsiloxanes, for example, polydimethylsiloxanes comprising trimethylsilyl end groups having a viscosity of from $5\times10^{-6}$ to 2.5 m$^2$/s at 25° C., for example, from $1\times10^{-5}$ to 1 m$^2$/s. The viscosity of the silicones is measured, for example, at 25° C. according to ASTM standard 445 Appendix C.

Non-limiting examples of these polyalkylsiloxanes include:
the Silbione oils of the 47 and 70 047 series and the Mirasil oils sold by Rhodia Chimie, for example, the oil 70 047 V 500 000;
the oils of the Mirasil series sold by the company Rhodia Chimie;
the oils of the 200 series from the company Dow Corning, such as DC200 with a viscosity of 60 000 cSt; and
the Viscasil oils from General Electric and certain oils of the SF series (SF 96, SF 18) from General Electric.

Further examples include, but are not limited to, polydimethylsiloxanes comprising dimethylsilanol end groups (Dimethiconol according to the CTFA name) such as the oils of the 48 series from the company Rhodia Chimie.

Suitable compounds in this category of polyalkylsiloxanes, include, for example, the products sold under the names Abil Wax 9800 and 9801 by the company Goldschmidt, which are poly($C_1$-$C_{20}$)alkylsiloxanes.

The polyalkylarylsiloxanes may be chosen from linear and/or branched polydimethylmethylphenylsiloxanes and polydimethyldiphenylsiloxanes having a viscosity ranging from $1\times10^{-5}$ to $5\times10^{-2}$ m$^2$/s at 25° C.

Non-limiting examples of these polyalkylarylsiloxanes include:
the Silbione oils of the 70 641 series from Rhodia Chimie;
the oils of the Rhodorsil 70 633 and 763 series from Rhodia Chimie;
the oil Dow Corning 556 Cosmetic Grade Fluid from Dow Corning;
the silicones of the PK series from Bayer, such as the product PK20;
the silicones of the PN and PH series from Bayer, such as the products PN1000 and PH1000; and
oils of the SF series from General Electric, such as SF 1023, SF 1154, SF 1250, and SF 1265.

Silicone gums that can be used in accordance with the present disclosure may include, for example, polydiorganosiloxanes with high number-average molecular masses ranging from 200 000 to 1 000 000, used alone or as a mixture in a solvent. This solvent may be chosen from volatile silicones, polydimethylsiloxane (PDMS) oils, polyphenylmethylsiloxane (PPMS) oils, isoparaffins, polyisobutylenes, methylene chloride, pentane, dodecane, tridecane, and mixtures thereof.

Examples of such polydiorganosiloxanes include, but are not limited to:
polydimethylsiloxane (PDMS),
polydimethylsiloxane/methylvinylsiloxane gums,
polydimethylsiloxane/diphenylsiloxane,
polydimethylsiloxane/phenylmethylsiloxane, and
polydimethylsiloxane/diphenylsiloxane/methylvinylsiloxane.

Further examples include mixtures of polydiorganosiloxanes, such as:
mixtures formed from a polydimethylsiloxane hydroxylated at the chain end (referred to as dimethiconol according to the nomenclature in the CTFA dictionary) and from a cyclic polydimethylsiloxane (referred to as cyclomethicone according to the nomenclature in the CTFA dictionary), such as the product Q2 1401 sold by the company Dow Corning;

mixtures formed from a polydimethylsiloxane gum with a cyclic silicone, such as the product SF 1214 Silicone Fluid from the company General Electric; this product is an SF 30 gum corresponding to a dimethicone, having a number-average molecular weight of 500 000, dissolved in the oil SF 1202 Silicone Fluid corresponding to decamethylcyclopentasiloxane;

mixtures of two PDMSs with different viscosities, for example, of a PDMS gum and a PDMS oil, such as the product SF 1236 from the company General Electric. The product SF 1236 is a mixture of an SE 30 gum defined above, having a viscosity of 20 m$^2$/s, and an SF 96 oil, with a viscosity of $5\times10^{-6}$ m$^2$/s. In at least one embodiment, this product may comprise 15% SE 30 gum and 85% SF 96 oil.

The organopolysiloxane resins that can be used in accordance with the present disclosure may include crosslinked siloxane systems comprising the following units:

$R_2SiO_{2/2}$, $R_3SiO_{1/2}$, $RSiO_{3/2}$, and $SiO_{4/2}$. in which R is chosen from hydrocarbon-based groups comprising from 1 to 16 carbon atoms and phenyl groups. Examples of these products include, but are not limited to, those in which R is chosen from $C_1$-$C_4$ lower alkyl radicals, for example, methyl and phenyl radicals.

These resins may also include, for example, the product sold under the name Dow Corning 593 and those sold under the names Silicone Fluid SS 4230 and SS 4267 by the company General Electric, which are silicones of dimethyl/trimethyl siloxane structure.

Further examples of resins include, but are not limited to, the trimethyl siloxysilicate type resins sold, for example, under the names X22-4914, X21-5034, and X21-5037 by the company Shin-Etsu.

The organomodified silicones that can be used in accordance with the present disclosure may be silicones as defined above and may comprise in their structure at least one organofunctional group attached via a hydrocarbon-based radical.

Examples of organomodified silicones include, but are not limited to:

polyethyleneoxy and/or polypropyleneoxy groups optionally comprising $C_6$-$C_{24}$ alkyl groups, such as the products known as dimethicone copolyol sold by the company Dow Corning under the name DC 1248 or the oils Silwet L 722, L 7500, L 77, and L 711 by the company Union Carbide, and the ($C_{12}$)alkylmethicone copolyol sold by the company Dow Corning under the name Q2 5200;

substituted or unsubstituted amine groups, such as the products sold under the name GP 4 Silicone Fluid and GP 7100 by the company Genesee, or the products sold under the names Q2 8220 and Dow Corning 929 and 939 by the company Dow Corning. The substituted amine groups may be chosen, for example, from $C_1$-$C_4$ aminoalkyl groups;

thiol groups such as the products sold under the names GP 72 A and GP 71 from Genesee;

alkoxylated groups such as the product sold under the name Silicone Copolymer F-755 by SWS Silicones and Abil Wax 2428, 2434, and 2440 by the company Goldschmidt;

hydroxylated groups such as polyorganosiloxanes comprising a hydroxyalkyl function, described, for example, in French Patent Application No. 85/16334, and corresponding to formula (XI):

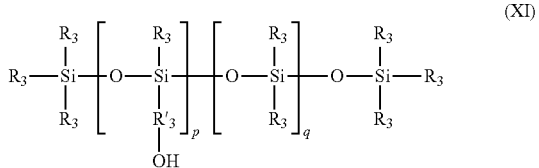

(XI)

in which the radicals $R_3$, which may be identical or different, are chosen from methyl and phenyl radicals; wherein at least 60 mol % of the radicals $R_3$ are methyl radicals;

the radical $R'_3$ is chosen from $C_2$-$C_{18}$ divalent hydrocarbon-based alkylene chain units;

p is a number ranging from 1 to 30; and q is a number ranging from 1 to 150;

acyloxyalkyl groups, for example, the polyorganosiloxanes described in U.S. Pat. No. 4,957,732 and corresponding to formula (XII):

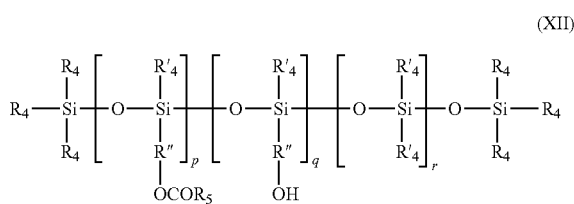

(XII)

in which:

$R_4$ is chosen from methyl, phenyl, —$OCR_5$, and hydroxyl groups, one of the radicals $R_4$ per silicon atom possibly being OH;

$R'_4$ is chosen from methyl and phenyl groups; at least 60 mol % of all the radicals $R_4$ and $R'_4$ being methyl groups;

$R_5$ is chosen from $C_8$-$C_{20}$ alkyl and alkenyl groups;

R" is chosen from $C_2$-$C_{18}$ linear or branched divalent hydrocarbon-based alkylene radicals;

r is an integer ranging from 1 to 120;

p is a integer ranging from 1 to 30;

q is equal to 0 or is less than 0.5 p, wherein the sum of p+q ranges from 1 to 30;

and wherein the polyorganosiloxanes of formula (XII) may comprise groups:

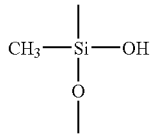

in proportions not exceeding 15% of the sum p+q+r;

anionic groups of carboxylic type, such as those present in the products described in European Patent No. 0 186 507 from the company Chisso Corporation, or of alkylcarboxylic type, such as those present in the product X-22-3701 E from the company Shin-Etsu; 2-hydroxyalkyl sulfonate; and 2-hydroxyalkyl thiosulfate such as the products sold by the company Goldschmidt under the names Abil S201 and Abil S255;

hydroxyacylamino groups, such as the polyorganosiloxanes described in European Patent Application No. 0 342 834, for example, of the product Q2-8413 from the company Dow Corning.

The composition according to the present disclosure may also comprise silicones comprising a polysiloxane portion and a portion comprising a non-silicone organic chain, one of the two portions constituting the main chain of the polymer, the other being grafted onto the main chain. These polymers are described, for example, in European Patent Application Nos. 0 412 704, 0 412 707, 0 640 105, and 0 582 152, International Patent Application Publication Nos. WO 95/00578 and WO 93/23009, and U.S. Pat. Nos. 4,693,935, 4,728,571, and 4,972,037. In at least one embodiment, these polymers may be anionic or nonionic.

Such polymers may be chosen, for example, from copolymers that can be obtained by free-radical polymerization starting with a monomer mixture comprising:

a) 50 to 90% by weight of tert-butyl acrylate;

b) 0 to 40% by weight of acrylic acid; and c) 5 to 40% by weight of silicone macromer of formula (XIII):

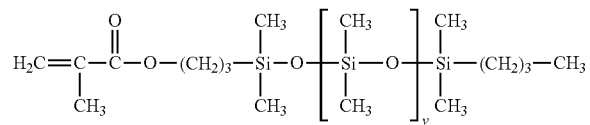

(XIII)

wherein v is a number ranging from 5 to 700; the weight percentages being calculated relative to the total weight of the monomers.

Other examples of grafted silicone polymers include, for example, polydimethylsiloxanes (PDMS) onto which are grafted, via a connecting chain unit of thiopropylene type, mixed polymer units of poly(meth)acrylic acid type and of polyalkyl(meth)acrylate type and polydimethylsiloxanes (PDMS) onto which are grafted, via a connecting chain unit of thiopropylene type, polymer units of polyisobutyl(meth) acrylate type.

According to one embodiment of the present disclosure, all of the silicones may be used in the form of emulsions, nanoemulsions, or microemulsions.

The polyorganosiloxanes used in accordance with the present disclosure may be chosen from:

non-volatile silicones chosen from the family of polyalkylsiloxanes comprising trimethylsilyl end groups, such as oils having a viscosity ranging from 0.2 to 2.5 m²/s at 25° C., such as the oils of the DC200 series from Dow Corning, for example, those with a viscosity of 60 000 cSt, of the Silbione 70047 and 47 series and the oil 70 047 V 500 000, which are sold by the company Rhodia Chimie, polyalkylsiloxanes comprising dimethylsilanol end groups, such as dimethiconols, and polyalkylarylsiloxanes such as the oil Silbione 70641 V 200 sold by the company Rhodia Chimie;

the organopolysiloxane resin sold under the name Dow Corning 593;

polysiloxanes comprising amine groups, such as amodimethicones and trimethylsilylamodimethicones.

The cationic proteins and cationic protein hydrolysates may be chosen from chemically modified polypeptides bearing quaternary ammonium groups at the end of the chain or grafted thereto. Their molecular mass can range, for example, from 1500 to 10 000, for example, from 2000 to 5000. Examples of these compounds include, but are not limited to:

collagen hydrolysates bearing triethylammonium groups, such as the products sold under the name Quat-Pro E by the company Maybrook and referred to in the CTFA dictionary as "Triethonium Hydrolyzed Collagen Ethosulfate";

collagen hydrolysates bearing trimethylammonium and trimethylstearylammonium chloride groups, sold under the name Quat-Pro S by the company Maybrook and referred to in the CTFA dictionary as "Steartrimonium Hydrolyzed Collagen";

animal protein hydrolysates bearing trimethylbenzylammonium groups such as the products sold under the name Crotein BTA by the company Croda and referred to in the CTFA dictionary as "Benzyltrimonium hydrolyzed animal protein";

protein hydrolysates bearing, on the polypeptide chain, quaternary ammonium groups comprising at least one alkyl radical comprising from 1 to 18 carbon atoms.

Non-limiting examples of protein hydrolysates include:

Croquat L in which the quaternary ammonium groups comprise a $C_{12}$ alkyl group;

Croquat M in which the quaternary ammonium groups comprise $C_{10}$-$C_{18}$ alkyl groups;

Croquat S in which the quaternary ammonium groups comprise a $C_{18}$ alkyl group; and Crotein Q in which the quaternary ammonium groups comprise at least one alkyl group comprising from 1 to 18 carbon atoms.

These various products are sold, for example, by the company Croda.

Other quaternized proteins or hydrolysates include, for example, those corresponding to formula (XIV):

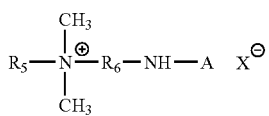

(XIV)

in which $X^-$ is an anion of an organic or mineral acid,

A is a protein residue derived from hydrolysates of collagen protein, $R_5$ is a lipophilic group comprising up to 30 carbon atoms, and $R_6$ is an alkylene group comprising from 1 to 6 carbon atoms. Non-limiting examples of such compounds include the products sold by the company Inolex under the name Lexein QX 3000, referred to in the CTFA dictionary as "Cocotrimonium Collagen Hydrolysate".

Further examples of quaternized proteins or hydrolysates include quaternized plant proteins such as wheat, corn, and soybean proteins. Suitable quaternized wheat proteins include, for example, those sold by the company Croda under the names Hydrotriticum WQ and QM, referred to in the CTFA dictionary as "Cocodimonium Hydrolysed Wheat Protein", Hydrotriticum QL, referred to in the CTFA dictionary as "Lauridimonium Hydrolysed Wheat Protein", and Hydrotriticum QS, referred to in the CTFA dictionary as "Steardimonium Hydrolysed Wheat Protein".

According to the present disclosure, the compounds of ceramide type may include, but are not limited to, natural or synthetic ceramides, glycoceramides, pseudoceramides, and/or neoceramides.

Compounds of ceramide type are described, for example, in German Patent Application Nos. 4 424 530, 4 424 533, 4 402 929, and 4 420 736, International Patent Application Publication Nos. WO 95/23807, WO 94/07844, WO 95/16665, WO 94/07844, WO 94/24097, and WO 94/10131, European Patent Application Nos. 0 646 572 and 0 227 994, and French Patent Application No. 2 673 179, the teachings of which are incorporated herein by reference.

Compounds of ceramide type may include, for example:
2-N-linoleoylaminooctadecane-1,3-diol,
2-N-oleoylaminooctadecane-1,3-diol,
2-N-palmitoylaminooctadecane-1,3-diol,
2-N-stearoylaminooctadecane-1,3-diol,
2-N-behenoylaminooctadecane-1,3-diol,
2-N-[2-hydroxypalmitoyl]aminooctadecane-1,3-diol,
2-N-stearoylaminooctadecane-1,3,4-triol, for example, N-stearoylphytosphingosine,
2-N-palmitoylaminohexadecane-1,3-diol,
bis(N-hydroxyethyl-N-cetyl)malonamide,
N-(2-hydroxyethyl)-N-(3-cetyloxy-2-hydroxypropyl)cetylamide,
N-docosanoyl-N-methyl-D-glucamine, and
mixtures thereof.

Cationic surfactants may also be used in accordance with the present disclosure, for example, optionally polyoxyalkylenated primary, secondary, or tertiary fatty amine salts; quaternary ammonium salts; imidazoline derivatives; and amine oxides of cationic nature.

Examples of quaternary ammonium salts include, but are not limited to:

those of general formula (XV):

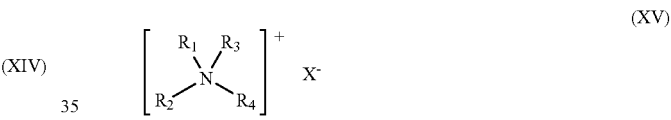

(XV)

in which the radicals $R_1$ to $R_4$, which may be identical or different, are chosen from linear or branched aliphatic radicals comprising from 1 to 30 carbon atoms, and aromatic radicals such as aryl and alkylaryl radicals. The aliphatic radicals may comprise hetero atoms such as oxygen, nitrogen, sulfur, and halogens. The aliphatic radicals may be chosen, for example, from alkyl, alkoxy, polyoxy($C_2$-$C_6$)alkylene, alkylamide, ($C_{12}$-$C_{22}$)alkylamido($C_2$-$C_6$)alkyl, ($C_{12}$-$C_{22}$)alkylacetate, and hydroxyalkyl radicals, comprising from 1 to 30 carbon atoms; and $X^-$ is an anion chosen from halides, phosphates, acetates, lactates, ($C_2$-$C_6$)alkyl sulfates, alkyl sulfonates, and alkylaryl sulfonates;

quaternary ammonium salts of imidazolinium, for example, the salt of formula (XVI) below:

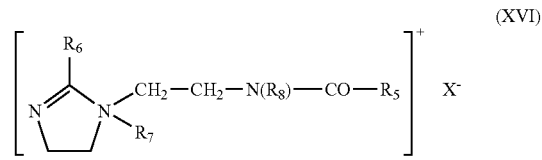

(XVI)

in which $R_5$ is chosen from alkenyl or alkyl radicals comprising from 8 to 30 carbon atoms, for example, tallow fatty acid derivatives, $R_6$ is chosen from hydrogen, $C_1$-$C_4$ alkyl radicals, and alkenyl or alkyl radicals comprising from 8 to 30 carbon atoms, $R_7$ is chosen from $C_1$-$C_4$ alkyl radicals, $R_8$ is chosen from hydrogen and $C_1$-$C_4$ alkyl radicals, and $X^-$ is an anion chosen from halides, phosphates, acetates, lactates, alkyl sulfates, alkyl sulfonates, and alkylaryl sulfonates.

In at least one embodiment, $R_5$ and $R_6$ may be a mixture of alkenyl or alkyl radicals comprising from 12 to 21 carbon atoms, for example, tallow fatty acid derivatives, $R_7$ may be a methyl radical, and $R_8$ may be hydrogen. Such a product is sold, for example, under the name "Rewoquat W 75" by the company Degussa;

diquaternary ammonium salts of formula (XVII):

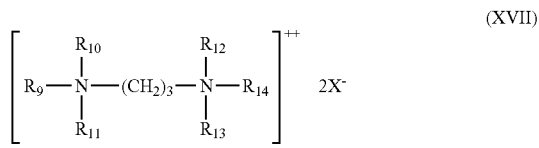

(XVII)

in which $R_9$ is chosen from aliphatic radicals comprising from 16 to 30 carbon atoms, $R_{10}$, $R_{11}$, $R_{12}$, $R_{13}$, and $R_{14}$, which may be identical or different, are chosen from hydrogen and alkyl radicals comprising from 1 to 4 carbon atoms, and $X^-$ is an anion chosen from halides, acetates, phosphates, nitrates, and methyl sulfates. Such diquaternary ammonium salts include, for example, propane tallow diammonium dichloride; and quaternary ammonium salts comprising at least one ester function.

The quaternary ammonium salts containing at least one ester function that may be used according to the present disclosure include, for example, those of formula (XVIII) below:

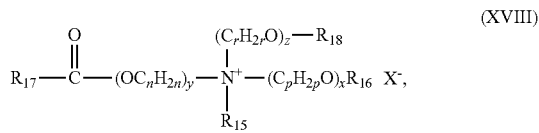

(XVIII)

in which:

$R_{15}$ is chosen from $C_1$-$C_6$ alkyl radicals and $C_1$-$C_6$ hydroxyalkyl or dihydroxyalkyl radicals;

$R_{16}$ is chosen from

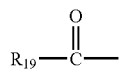

radicals, linear or branched, saturated or unsaturated $C_1$-$C_{22}$ hydrocarbon-based radicals $R_{20}$, and hydrogen, $R_{18}$ is chosen from

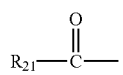

radicals, linear or branched, saturated or unsaturated $C_1$-$C_6$ hydrocarbon-based radicals $R_{22}$, and hydrogen, $R_{17}$, $R_{19}$, and $R_{21}$, which may be identical or different, are chosen from linear or branched, saturated or unsaturated $C_7$-$C_{21}$ hydrocarbon-based radicals;

n, p, and r, which may be identical or different, are integers ranging from 2 to 6;

y is an integer ranging from 1 to 10;

x and z, which may be identical or different, are integers ranging from 0 to 10; and $X^-$ is a simple or complex, organic or inorganic anion; with the proviso that the sum x+y+z ranges from 1 to 15, that when x is 0, then $R_{16}$ denotes $R_{20}$, and that when z is 0, then $R_{18}$ denotes $R_{22}$.

In one embodiment, the $R_{15}$ alkyl radicals may be linear or branched. In another embodiment, the $R_{15}$ radicals may be linear.

The $R_{15}$ radicals may be chosen from methyl, ethyl, hydroxyethyl, and dihydroxypropyl radicals. In one embodiment, the $R_{15}$ radicals may be chosen from methyl and ethyl radicals.

In another embodiment, the sum x+y+z may range from 1 to 10.

When $R_{16}$ is a hydrocarbon-based radical $R_{20}$, it may be long and comprise from 12 to 22 carbon atoms, or short and comprise from 1 to 3 carbon atoms.

When $R_{18}$ is a hydrocarbon-based radical $R_{22}$, it may comprise from 1 to 3 carbon atoms.

In one embodiment, $R_{17}$, $R_{19}$, and $R_{21}$, which may be identical or different, may be chosen from linear or branched, saturated or unsaturated $C_{11}$-$C_{21}$ hydrocarbon-based radicals, for example, linear or branched, saturated or unsaturated, $C_{11}$-$C_{21}$ alkyl and alkenyl radicals.

In another embodiment, x and z, which may be identical or different, may be equal to 0 or 1, y may be equal to 1, and n, p, and r, which may be identical or different, may be equal to 2 or 3, for instance, equal to 2.

The anion may be chosen from halides (for example, chloride, bromide, and iodide) and alkyl sulfates, for example, methyl sulfate. However, methanesulfonate, phosphate, nitrate, tosylate, an anion derived from an organic acid, such as acetate or lactate, or any other anion that is compatible with the ammonium containing an ester function, may be used.

In one embodiment, the anion $X^-$ may be chosen from chloride and methyl sulfate.

In another embodiment, the ammonium salts may be those of formula (XVIII) in which:

$R_{15}$ is chosen from methyl and ethyl radicals, x and y are equal to 1;

z is equal to 0 or 1;

n, p, and r are equal to 2;

$R_{16}$ is chosen from

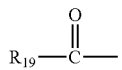

radicals, methyl radicals, ethyl radicals, $C_{14}$-$C_{22}$ hydrocarbon-based radicals, and hydrogen;

$R_{18}$ is chosen from

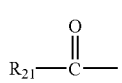

radicals and hydrogen; and $R_{17}$, $R_{19}$, and $R_{21}$, which may be identical or different, are chosen from linear or branched, saturated or unsaturated $C_{13}$-$C_{17}$ hydrocarbon-based radicals, for example, linear or branched, saturated or unsaturated $C_{13}$-$C_{17}$ alkyl and alkenyl radicals.

In at least one embodiment, the hydrocarbon-based radicals may be linear.

Examples that may be mentioned include the compounds of formula (XVI) such as the diacyloxyethyldimethylammonium, diacyloxyethylhydroxyethylmethyl-ammonium, monoacyloxyethyidihydroxyethylmethylammonium, triacyloxyethylmethylammonium, and monoacyloxyethylhydroxyethyidimethylammonium salts (for example, chloride and methyl sulfate), and mixtures thereof. The acyl radicals may comprise from 14 to 18 carbon atoms and may be obtained from a plant oil such as palm oil and sunflower oil. When the compound comprises several acyl radicals, these radicals may be identical or different.

These products may be obtained, for example, by direct esterification of triethanolamine, triisopropanolamine, an alkyldiethanolamine, or an alkyldiisopropanolamine, which are optionally oxyalkylenated, with fatty acids or with fatty acid mixtures of plant or animal origin, or by transesterification of the methyl esters thereof. This esterification may be followed by a quaternization using an alkylating agent such as an alkyl halide (for example, methyl and ethyl halide), a dialkyl sulfate (for example, dimethyl and or diethyl sulfate), methyl methanesulfonate, methyl para-toluenesulfonate, glycol chlorohydrin, and glycerol chlorohydrin.

Such compounds are sold, for example, under the names Dehyquart by the company Cognis, Stepanquat by the company Stepan, Noxamium by the company CECA, and Rewoquat WE 18 by the company Degussa.

Ammonium salts comprising at least one ester function, such as those described in U.S. Pat. Nos. 4,874,554 and 4,137,180.

Examples of quaternary ammonium salts of formula (XV) include, but are not limited to, tetraalkylammonium chlorides such as dialkyldimethylammonium chlorides and alkyltrimethylammonium chlorides, in which the alkyl radical comprises from 12 to 22 carbon atoms, for instance, behenyltrimethylammonium chloride, distearyidimethyl-ammonium chloride, cetyltrimethylammonium chloride, and benzyldimethylstearylammonium chloride, and stearamidopropyidimethyl(myristyl acetate)-ammonium chloride sold under the name Ceraphyl 70 by the company Van Dyk.

The fatty acids may be chosen from myristic acid, palmitic acid, stearic acid, behenic acid, oleic acid, linoleic acid, linolenic acid, and isostearic acid.

The fatty acid derivatives may be carboxylic acid esters, for example, mono-, di-, tri-, and tetracarboxylic esters.

The monocarboxylic acid esters may include, for example, linear or branched, saturated or unsaturated $C_1$-$C_{26}$ aliphatic acid monoesters of linear or branched, saturated or unsaturated, $C_1$-$C_{26}$ aliphatic alcohols, the total carbon number of these esters being greater than or equal to 10.

Examples of monoesters include, but are not limited to, dihydroabietyl behenate; octyidodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, and 2-octyidodecyl myristate, hexyl stearate, butyl stearate, isobutyl stearate; dioctyl malate, hexyl laurate, 2-hexyldecyl laurate, isostearyl neopentanoate, and isodecyl neopentanoate.

$C_4$-$C_{22}$ di- or tricarboxylic acid esters of $C_1$-$C_{22}$ alcohols and mono-, di- or tricarboxylic acid esters of $C_2$-$C_{26}$ di-, tri-, tetra-, or pentahydroxy alcohols may also be used in accordance with the present invention.

Non-limiting examples of such esters include, diethyl sebacate; diisopropyl sebacate; diisopropyl adipate; di-n-propyl adipate; dioctyl adipate; diisostearyl adipate; dioctyl maleate; glyceryl undecylenate; octyidodecylstearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate dicaprate; tridecyl erucate; triisopropyl citrate; triisostearyl citrate; glyceryl trilactate; glyceryl trioctanoate; trioctyldodecyl citrate; and trioleyl citrate.

In at least one embodiment, the esters may be chosen from ethyl and isopropyl palmitates, 2-ethylhexyl palmitate, 2-octyldecyl palmitate, alkyl myristates such as isopropyl, butyl, cetyl, and 2-octyldodecyl myristate, hexyl stearate, butyl stearate, isobutyl stearate; dioctyl malate, hexyl laurate, 2-hexyldecyl laurate, isononyl isononanoate, cetyl octanoate, isostearyl neopentanoate, and isodecyl neopentanoate.

The fluoro oils include, for example, the perfluoropolyethers described, for instance, in European Patent Application No. 0 486 135, which is incorporated herein by reference in its entirety, and the fluorohydrocarbon compounds described, for example, in International Patent Application Publication No. WO 93/11103, which is incorporated herein by reference in its entirety.

As used herein, the term "fluorohydrocarbon compounds" denotes compounds whose chemical structure contains a carbon skeleton in which certain hydrogen atoms have been replaced with fluorine atoms.

The fluoro oils may also be fluorocarbons such as fluoroamines, for example, perfluorotributylamine; and fluorohydrocarbons, for instance, perfluorodecahydronaphthalene, fluoro esters, and fluoro ethers.

Suitable perfluoropolyethers are sold, for example, under the trade names Fomblin by the company Montefluos and Krytox by the company Du Pont.

Additional examples of fluorohydrocarbon compounds include fluorine-containing fatty acid esters such as the product sold under the name Nofable OF by the company Nippon Oil.

In accordance with at least one embodiment of the present disclosure, a mixture of conditioning agents may also be used.

According to the present disclosure, the at least one conditioning agent may be present in the composition in an amount ranging from 0.001% to 20% by weight, for example, from 0.01% to 10% by weight, or from 0.1% to 3% by weight, relative to the total weight of the final composition.

Surfactants

The compositions of the present disclosure may comprise at least one surfactant, which may be present in the composition in an amount ranging from 0.1% to 60% by weight, for example, from 1% to 40%, or from 5% to 30%, relative to the total weight of the composition.

The at least one surfactant may be chosen from anionic, amphoteric and nonionic surfactants, and mixtures thereof.

Examples of surfactants that are suitable for use in accordance with the present disclosure include, but are not limited to:

(i) Anionic Surfactants:

In the context of the present disclosure, the nature of the anionic surfactant does not represent a truly critical factor.

Thus, examples of anionic surfactants which can be used, alone or as mixtures, in the context of the present disclosure, include salts (for example, alkaline salts, sodium salts, ammonium salts, amine salts, amino alcohol salts, and magnesium salts) of alkyl sulfates, alkyl ether sulfates, alkylamido ether sulfates, alkylarylpolyether sulfates, monoglyceride sulfates; alkyl sulfonates, alkyl phosphates, alkylamide sulfonates, alkylaryl sulfonates, α-olefin sulfonates, paraffin sulfonates; alkyl sulfosuccinates, alkyl ether sulfosuccinates, alkylamide sulfosuccinates; alkyl sulfosuccinamates; alkyl sulfoacetates; alkyl ether phosphates; acyl sarcosinates; acyl isethionates, and N-acyltaurates, the alkyl or acyl radical of all of these various compounds comprising, for example, from 8 to 24 carbon atoms, and the aryl radical, in at least one embodiment, being chosen from phenyl and benzyl groups. Fatty acid salts may also be used as anionic surfactants, such as the salts of oleic, ricinoleic, palmitic and stearic acids, coconut oil acid, and hydrogenated coconut oil acid; and acyl lactylates in which the acyl radical comprises from 8 to 20 carbon atoms. Weakly anionic surfactants may also be used, such as alkyl-D-galactosiduronic acids and their salts, as well as polyoxyalkylenated ($C_6$-$C_{24}$) alkyl ether carboxylic acids, polyoxyalkylenated ($C_6$-$C_{24}$) alkylaryl ether carboxylic acids, polyoxyalkylenated ($C_6$-$C_{24}$) alkylamido ether carboxylic acids and their salts, for example, those comprising from 2 to 50 ethylene oxide groups, and mixtures thereof.

In at least one embodiment of the present disclosure, the anionic surfactants may be chosen from alkyl sulfate salts, alkyl ether sulfate salts, and mixtures thereof.

(ii) Nonionic Surfactants:

Nonionic surfactants are compounds that are generally well known in the art (see for example in this respect "Handbook of Surfactants" by M. R. Porter, published by Blackie & Son (Glasgow and London), 1991, pp. 116-178) and, in the context of the present disclosure, their nature is not a critical feature. Thus, they may be chosen, for example, from polyethoxylated, polypropoxylated, or polyglycerolated fatty acids, alkylphenols, α-diols, and alcohols having a fatty chain comprising, for example, from 8 to 18 carbon atoms, it being possible for the number of ethylene oxide or propylene oxide groups to range, for example, from 2 to 50, and for the number of glycerol groups to range, for example, from 2 to 30. Further examples of nonionic surfactants may include copolymers of ethylene oxide and of propylene oxide, condensates of ethylene oxide and of propylene oxide with fatty alcohols; polyethoxylated fatty amides having, for example, from 2 to 30 mol of ethylene oxide, polyglycerolated fatty amides containing on average from 1 to 5, for example, from 1.5 to 4, glycerol groups; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as ($C_{10}$-$C_{14}$)alkylamine oxides, and N-acylaminopropylmorpholine oxides. In at least one embodiment, the nonionic surfactants may be chosen from alkylpolyglycosides.

(iii) Amphoteric Surfactant(s):

The amphoteric surfactants, whose nature is not a critical feature in the context of the present disclosure, may be, for example, aliphatic secondary or tertiary amine derivatives in which the aliphatic radical is a linear or branched chain comprising from 8 to 22 carbon atoms and comprising at least one water-soluble anionic group (for example, carboxylate, sulfonate, sulfate, phosphate, and phosphonate). Suitable amphoteric surfactant may also include, for example, ($C_8$-$C_{20}$)alkylbetaines, sulfobetaines, ($C_8$-$C_{20}$)alkylamido($C_1$-$C_6$)alkylbetaines, and ($C_8$-$C_{20}$)alkylamido($C_1$-$C_6$)alkylsulfobetaines.

Examples of amine derivatives include, but are not limited to, the products sold under the name Miranol, and described in U.S. Pat. Nos. 2,528,378 and 2,781,354, and having the structures (2) and (3) below:

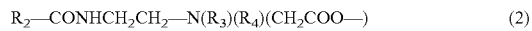

$$R_2\text{—CONHCH}_2\text{CH}_2\text{—N}(R_3)(R_4)(\text{CH}_2\text{COO—}) \quad (2)$$

in which:

$R_2$ is chosen from alkyl radicals derived from an acid $R_2$—COOH present in hydrolysed coconut oil, heptyl radicals, nonyl radicals, and undecyl radicals, $R_3$ is a β-hydroxyethyl group, and $R_4$ is a carboxymethyl group;

and

$$R_5\text{—CONHCH}_2\text{CH}_2\text{—N(B)(D)} \quad (3)$$

in which:

B is —$CH_2CH_2OX'$,

D is —$(CH_2)_z$—Y', with z=1 or 2,

X' is chosen from —$CH_2CH_2$—COOH and hydrogen,

Y' is chosen from —COOH and —$CH_2$—CHOH—$SO_3H$, and $R_5$ is chosen from alkyl radicals of an acid $R_5$—COOH present in coconut oil or in hydrolysed linseed oil, alkyl radicals, for example, $C_7$, $C_9$, $C_{11}$ and $C_{13}$ alkyl radicals, $C_{17}$ alkyl radicals and their iso forms, and unsaturated $C_{17}$ radicals.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylampho-dipropionate, disodium caryloamphodipropionate, lauroamphodipropionic acid, and cocoamphodipropionic acid.

A non-limiting example of a suitable commercial product is the cocoamphodiacetate sold under the trade name Miranol C2M Concentrate by the company Rhodia Chimie.

In at least one embodiment of the present disclosure, mixtures of surfactants may be used, for example, mixtures of anionic surfactants and mixtures of anionic surfactants and of amphoteric or nonionic surfactants. In another embodiment, the at least one surfactant is a mixture comprising at least one anionic surfactant and at least one amphoteric surfactant.

In such a mixture, the anionic surfactant may be chosen from sodium, triethanolamine or ammonium ($C_{12}$-$C_{14}$)alkyl sulfates; sodium, triethanolamine, or ammonium ($C_{12}$-$C_{14}$) alkyl ether sulfates oxyethylenated with 2.2 mol of ethylene oxide; sodium cocoyl isethionate; sodium α-($C_{14}$-$C_{16}$)olefin sulfonate; and mixtures thereof, with:

either an amphoteric surfactant such as the amine derivatives known as disodium cocoamphodipropionate or sodium cocoamphopropionate, sold, for example, by the company Rhodia Chimie under the trade name Miranol C2M CONC as an aqueous solution containing 38% active material, or under the name Miranol C32;

or an amphoteric surfactant of zwitterionic type such as alkylbetaines, for example, the cocobetaine sold under the name Dehyton AB 30 as an aqueous solution containing 32% AM by the company Cognis.

Additives

The composition of the present disclosure may also comprise at least one additive chosen from thickeners, fragrances, nacreous agents, preserving agents, anionic or nonionic polymers, non-cationic proteins, non-cationic protein hydrolysates, 18-methyleicosanoic acid, hydroxy acids, polymers other than those of the present disclosure, for example, polyether nonionic or cationic associative polyurethanes, and any other additive conventionally used in cosmetics that does not substantially affect the properties of the compositions according to the present disclosure.

These additives may be present in the composition according to the present disclosure in amounts ranging from 0 to 20% by weight relative to the total weight of the composition. The precise amount of each additive is readily determined by a person skilled in the art, depending on its nature and its function.

The compositions in accordance with the present disclosure may be used for washing and/or treating keratin fibers such as the hair.

The compositions according to the present disclosure may be shampoos. In this embodiment of the present disclosure, the compositions may comprise a washing base, which is generally aqueous. The at least one surfactant forming the washing base may be chosen without preference, alone or as mixtures, from the anionic, amphoteric, and nonionic surfactants as defined above. The quantity and quality of the washing base are chosen so as to give the composition satisfactory foaming power and/or detergent power. Thus, according to the present disclosure, the washing base may be present in the composition in an amount ranging from 4% to 50% by weight, for example, from 6% to 35% by weight, or from 8% to 25% by weight relative to the total weight of the composition. In at least one embodiment, the washing base may comprise at least 3% by weight, for example, from 4% to 30% by weight of anionic surfactant relative to the total weight of the composition.

The compositions of the present disclosure may also be in the form of leave-in or rinse-out hair conditioners; or in the form of a composition to be applied after dyeing, bleaching, permanent-waving and/or relaxing the hair, or alternatively, between the two steps of a permanent-waving or hair-relaxing operation.

The compositions according to the present disclosure may be in the form of aqueous or aqueous-alcoholic haircare lotions. The cosmetic compositions according to the present disclosure may also be in the form of a gel, a milk, a cream, an emulsion, or a mousse, and may be used on the hair.

The compositions may be packaged in various forms, for example, in vaporizers, pump-dispenser bottles, and in aerosol containers, in order to apply the composition in vaporized form or in the form of a mousse. Such packaging forms are indicated, for example, when it is desired to obtain a spray, a lacquer, or a mousse for treating the hair.

The pH of the composition applied to the keratin fibers may generally range from 1 to 11. In at least one embodiment, the pH may range from 2 to 6, and may be adjusted to the desired value by means of acidifying or basifying agents that are well known in the prior art for compositions applied to keratin fibers.

Examples of basifying agents include, but are not limited to, aqueous ammonia; alkali metal carbonates; alkanolamines such as monoethanolamine, diethanolamine, triethanolamine, and derivatives thereof; oxyethylenated and/or oxypropylenated hydroxyalkylamines and ethylenediamines; sodium hydroxide; potassium hydroxide; and compounds of formula (XX):

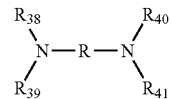

in which:

R is a propylene residue optionally substituted with an entity chosen from hydroxyl and $C_1$-$C_4$ alkyl radicals; and $R_{38}$, $R_{39}$, $R_{40}$, and $R_{41}$, which may be identical or different, are chosen from hydrogen, $C_1$-$C_4$ alkyl radicals, and $C_1$-$C_4$ hydroxyalkyl radicals.

The acidifying agents may include, for example, mineral or organic acids, for instance hydrochloric acid, orthophosphoric acid, carboxylic acids, for instance tartaric acid, citric acid, and lactic acid, and sulfonic acids.

METHODS

Disclosed herein is a method for treating keratin fibers such as the hair, comprising applying to the keratin materials a cosmetic composition as defined above, and then in optionally rinsing with water.

According to one embodiment, the compositions according to the present disclosure will be used as compositions for treating keratin fibers, for example, hair dyed by direct dyeing or oxidation dyeing.

Also disclosed herein is a method for the post-treatment of an oxidation dyeing or direct dyeing operation on keratin fibers such as the hair, comprising applying to the keratin materials a cosmetic composition as defined above.

Further disclosed herein is a method for dyeing keratin fibers comprising applying to the keratin fibers, such as the hair, a direct or oxidation dye composition (A) for a time that is sufficient to develop the color, and, after optionally rinsing and optionally drying, applying a composition (B) comprising a composition according to the present disclosure as defined above.

As indicated above, the post-treatment composition according to the present disclosure may be applied immediately after dyeing, or the application may be delayed. As used herein, the term "delayed" means an application that takes place up to a few hours, one day, or several days (for example, from 1 to 60 days) after the dyeing operation.

In at least one embodiment, several applications of the composition of the present disclosure may be performed between two colorations, for example, the number of applications between two colorations may range from 1 to 60, or from 2 to 30.

The post-treatment composition may be used in rinse-out or leave-in mode, i.e., its application may or may not be followed by rinsing.

In the first case, the leave-in time of the post-treatment composition may range from a few seconds to 90 minutes, for example, from 30 seconds to 20 minutes.

The temperature at which the post-treatment composition is applied may range from 10° C. to 70° C., for example, from 10 to 60° C., or at room temperature.

In accordance with the present disclosure, the nature and concentration of the dyes present in the dye compositions is not critical.

In the case of lightening direct dyeing operations, the dye composition (A) may result from the mixing, at the time of use, of a dye composition (A1) comprising at least one direct dye and a composition (A2) comprising at least one oxidizing agent.

In the case of oxidation dyeing, the dye composition (A) may result from the mixing, at the time of use, of a dye composition (A1) comprising at least one oxidation base and optionally at least one coupler and/or a direct dye and of a composition (A2) comprising at least one antioxidant.

Direct Dyes

The direct dyes may be compounds that absorb light radiation in the visible range (400-750 nm). They may be chosen from nonionic, anionic, and cationic direct dyes.

Generally, the direct dyes may be chosen from nitrobenzene dyes and azo, anthraquinone, naphthoquinone, benzoquinone, phenothiazine, indigoid, xanthene, phenanthridine, phthalocyanin, and triarylmethane-based dyes, and mixtures thereof.

Examples of suitable nitrobenzene dyes include red and orange compounds, for instance, 1-hydroxy-3-nitro-4-N-(γ-hydroxypropyl)aminobenzene, N-(β-hydroxyethyl)amino-3-nitro-4-aminobenzene, 1-amino-3-methyl-4-N-(β-hydroxyethyl)amino-6-nitrobenzene, 1-hydroxy-3-nitro-4-N-(β-hydroxyethyl)-aminobenzene, 1,4-diamino-2-nitrobenzene, 1-amino-2-nitro-4-methylaminobenzene, N-(β-hydroxyethyl)-2-nitroparaphenylenediamine, 1-amino-2-nitro-4-(β-hydroxyethyl)amino-5-chlorobenzene, 2-nitro-4-aminodiphenylamine, 1-amino-3-nitro-6-hydroxybenzene, 1-(β-aminoethyl)amino-2-nitro-4-(β-hydroxyethyloxy)benzene, 1-(β,γ-dihydroxypropyl)oxy-3-nitro-4-(β-hydroxyethyl)aminobenzene, 1-hydroxy-3-nitro-4-aminobenzene, 1-hydroxy-2-amino-4,6-dinitrobenzene, 1-methoxy-3-nitro-4-(β-hydroxyethyl)aminobenzene, 2-nitro-4'-hydroxydiphenylamine, 1-amino-2-nitro-4-hydroxy-5-methylbenzene, and mixtures thereof.

Other examples of nitrobenzene direct dyes include yellow and green dyes, for instance 1-β-hydroxyethyloxy-3-methylamino-4-nitrobenzene, 1-methylamino-2-nitro-5-(β, γ-dihydroxypropyl)oxybenzene, 1-(β-hydroxyethyl)amino-2-methoxy-4-nitrobenzene, 1-(β-aminoethyl)amino-2-nitro-5-methoxybenzene, 1,3-bis(β-hydroxyethyl)amino-4-nitro-6-chlorobenzene, 1-amino-2-nitro-6-methylbenzene, 1-(β-hydroxyethyl)amino-2-hydroxy-4-nitrobenzene, N-(β-hydroxyethyl)-2-nitro-4-trifluoromethylaniline, 4-(β-hydroxy-ethyl)amino-3-nitrobenzenesulfonic acid, 4-ethylamino-3-nitrobenzoic acid, 4-β-hydroxyethyl)amino-3-nitrochlorobenzene, 4-(β-hydroxyethyl)amino-3-nitromethyl-benzene, 4-(β,γ-dihydroxypropyl)amino-3-nitrotrifluoromethylbenzene, 1-(β-ureidoethyl)amino-4-nitrobenzene, 1,3-diamino-4-nitrobenzene, 1-hydroxy-2-amino-5-nitrobenzene, 1-amino-2-[tris(hydroxymethyl)methyl]amino-5-nitrobenzene, 1-(β-hydroxyethyl)amino-2-nitrobenzene, and 4-(β-hydroxyethyl)amino-3-nitrobenzamide.

Blue and violet nitrobenzene dyes may also be used, for instance, 1-(β-hydroxyethyl)amino-4-N, N-bis(β-hydroxyethyl)amino-2-nitrobenzene, 1-(γ-hydroxypropyl)amino-4-N,N-bis(β-hydroxyethyl)amino-2-nitrobenzene, 1-(β-hydroxy-ethyl)amino-4-(N-methyl, N-β-hydroxyethyl)amino-2-nitrobenzene, 1-(β-hydroxyethyl)amino-4-(N-ethyl, N-β-hydroxyethyl)amino-2-nitrobenzene, 1-(β,γ-dihydroxypropyl)amino-4-(N-ethyl, N-β-hydroxyethyl) amino-2-nitrobenzene, the 2-nitro-para-phenylenediamines of the following formula:

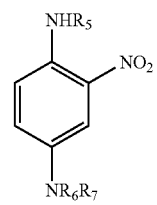

in which:

$R_6$ is chosen from $C_1$-$C_4$ alkyl radicals, β-hydroxyethyl radicals, β-hydroxypropyl radicals, and γ-hydroxypropyl radicals;

$R_5$ and $R_7$, which may be identical or different, are chosen from β-hydroxyethyl, β-hydroxypropyl, γ-hydroxypropyl, and β,γ-dihydroxypropyl radicals, with the proviso that at least one of the radicals $R_5$, $R_6$, or $R_7$ is a γ-hydroxypropyl radical and that $R_6$ and $R_7$ are not simultaneously β-hydroxyethyl radicals when $R_6$ is a γ-hydroxypropyl radical, such as those described in French Patent No. 2 692 572.

As is well known in the art, azo dyes are compounds comprising in their structure at least one —N═N— sequence not included in a ring; methine dyes are compounds comprising in their structure at least one —C═C— sequence not included in a ring; and azomethine dyes are compounds comprising in their structure at least one —C═N— sequence not included in a ring.

The triarylmethane-based dyes comprise in their structure at least one sequence below:

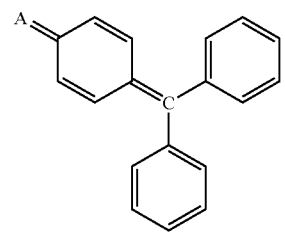

A denoting an oxygen or nitrogen atom.

The xanthene dyes comprise in their structure at least one sequence of formula:

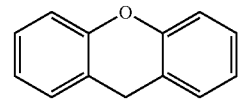 [SMILES: c1ccc2c(c1)Cc1ccccc1O2]

The phenanthridine dyes comprise in their structure at least one sequence of formula:

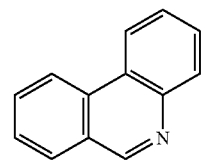 [SMILES: c1ccc2c(c1)cnc1ccccc12]

The phthalocyanin dyes comprise in their structure at least one sequence of formula:

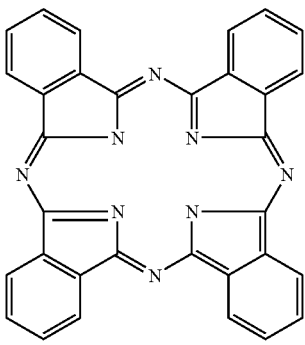 [SMILES: c1ccc2c(c1)-c1nc-2nc2[nH]c(nc3nc(nc4[nH]c(n1)c1ccccc41)-c1ccccc1-3)c1ccccc21]

The phenothiazine dyes comprise in their structure at least one sequence below:

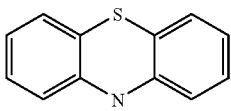

The direct dyes may moreover be chosen from basic dyes such as those listed in the Color Index, 3rd edition, for example, under the names "Basic Brown 16", "Basic Brown 17", "Basic Yellow 57", "Basic Red 76", "Basic Violet 10", "Basic Blue 26", and "Basic Blue 99"; from the acidic direct dyes listed in the Color Index, 3rd edition, under the names "Acid Orange 7", "Acid Orange 24", "Acid Yellow 36", "Acid Red 33", "Acid Red 184", "Acid Black 2", "Acid Violet 43", and "Acid Blue 62", and cationic direct dyes such as those described in International Patent Application Publication Nos. WO 95/01772 and WO 95/15144 and European Patent No. 0 714 954, which are incorporated herein by reference in their entireties.

When present, the at least one direct dye may be present in the composition in an amount ranging from 0.0005% to 12% by weight, for example, from 0.005% to 6% by weight relative to the total weight of the composition.

Oxidation Bases

The oxidation bases may be chosen from the oxidation bases conventionally used in oxidation dyeing, for example, para-phenylenediamines, bis(phenyl)alkylenediamines, para-aminophenols, ortho-aminophenols, and heterocyclic bases.

Non-limiting examples of para-phenylenediamines include para-phenylene-diamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetyl-aminoethyloxy-para-phenylenediamine, N-(β-methoxyethyl)-para-phenylenediamine, and the acid addition salts thereof.

In at least one embodiment, the para-phenylenediamines may be chosen from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and the acid addition salts thereof.

Suitable bis(phenyl)alkylenediamines include, for example, N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,5-dioxaoctane, and the acid addition salts thereof with an acid.

Examples of para-aminophenols include, but are not limited to, para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl) phenol, 4-amino-2-fluorophenol, and the acid addition salts thereof.

Non-limiting examples of ortho-aminophenols include 2-aminophenol, 2-amino-5-methylphenol, 2-amino-6-methylphenol, 5-acetamido-2-aminophenol, and the acid addition salts thereof.

Suitable heterocyclic bases include, for example, pyridine derivatives, pyrimidine derivatives, and pyrazole derivatives.

Pyridine derivatives may be chosen, for example, from the compounds described, for instance, in British Patent Nos. 1 026 978 and 1 153 196, as well as 2,5-di-aminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diamino-pyridine, and the acid addition salts thereof.

Examples of pyrimidine derivatives include, but are not limited to, the compounds described, for example, in German Patent No. 2 359 399; Japanese Patent Application No. 88-169 571; Japanese Patent No. 05-163 124; European Patent No. 0 770 375, and International Patent Application Publication No. WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in French Patent Application No. 2 750 048, for example, pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino) ethanol, 2-(7-aminopyrazolo[1,5-a]pyrimidin-3-ylamino)ethanol, 2-[(3-amino-pyrazolo[1,5-a]pyrimidin-7-yl)(2-hydroxyethyl)amino]ethanol, 2-[(7-aminopyrazolo[1,5-a]-pyrimidin-3-yl) (2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethyl-pyrazolo[1,5-a]pyrimidine-3,7-diamine, 3-amino-5-methyl-7-imidazolylpropylaminopyrazolo[1,5-a]pyrimidine, the acid addition salts thereof, and the tautomeric forms thereof, when a tautomeric equilibrium exists.

Non-limiting examples of pyrazole derivatives include the compounds described, for example, in German Patent Nos. 3 843 892 and 4 133 957, International Patent Application Publication Nos. WO 94/08969 and WO 94/08970, French Patent Application No. 2 733 749, and German Patent Application No. 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethel)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethyl-pyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the acid addition salts thereof.

When present, the at least one oxidation base may be present in the composition in an amount ranging from 0.0005% to 12% by weight, for example, from 0.005% to 6% by weight relative to the total weight of the dye composition.

Couplers

The oxidation dye compositions in accordance with the present disclosure may also comprise at least one coupler and/or at least one direct dye, for example, to modify the shades and/or to enrich them with tints.

The at least one coupler may be chosen from the couplers conventionally used in oxidation dyeing, for example, meta-phenylenediamines, meta-aminophenols, meta-diphenols, naphthols, and heterocyclic couplers, for instance, indole derivatives, indoline derivatives, pyridine derivatives, indazole derivatives, pyrazolo[1,5-b]-1,2,4-triazole derivatives, pyrazolo[3,2-c]-1,2,4-triazole derivatives, benzimidazole derivatives, benzothiazole derivatives, benzoxazole derivatives, 1,3-benzodioxole derivatives, pyrazolones, and the acid addition salts thereof.

Non-limiting examples of suitable couplers may include 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 2-methyl-1-naphthol, 6-hydroxyindole, 4-hydroxyindole, 4-hydroxy-N-methyl-indole, 6-hydroxyindoline, 6-hydroxybenzomorpholine, 3,5-diamino-2,6-dimethoxy-pyridine, 1-N(β-hydroxyethyl)amino-3,4-methylenedioxy-benzene, 2,6-bis(β-hydroxy-ethylamino) toluene, 2,6-dihydroxy-4-methylpyridine, 1H-3-methylpyrazol-5-one, 1-phenyl-3-methylpyrazol-5-one, and the acid addition salts thereof.

When present, the at least one coupler may be present in the composition in an amount ranging from 0.0001% to 10% by weight, for example, from 0.005% to 5% by weight relative to the total weight of the dye composition.

Adjuvants

The dye composition in accordance with the present disclosure may also contain various adjuvants conventionally used in hair dye compositions, such as anionic surfactants, cationic surfactants, nonionic surfactants, amphoteric surfactants, zwitterionic surfactants, and mixtures thereof; anionic polymers, cationic polymers, nonionic polymers, amphoteric polymers, zwitterionic polymers, and mixtures thereof; mineral thickeners; organic thickeners; antioxidants; penetrants; sequestrants; fragrances; buffers; dispersants; conditioning agents, for instance silicones; film-forming agents; preserving agents; and opacifiers.

It is understood that a person skilled in the art will take care to select the at least one optional additional compound such that the advantageous properties intrinsically associated with the oxidation dye composition in accordance with the present disclosure are not, or are not substantially, adversely affected by the envisaged addition.

The dye composition according to the present disclosure may be in various forms, such as in the form of liquids, creams or gels, or in any other form that is suitable for dyeing keratin fibers, such as human hair.

Oxidizing Agents

In accordance with the present disclosure the nature of the oxidizing agent used in the lightening direct dyeing operation (direct dyeing with an oxidizing agent) or in the oxidation dyeing operation is not critical.

The oxidizing agent may be chosen, for example, from hydrogen peroxide, urea peroxide, alkali metal bromates and ferricyanides, and persalts such as perborates and persulfates. The oxidizing agent may also be chosen from redox enzymes such as laccases, peroxidases, and two-electron oxidoreductases (such as uricase), where appropriate in the presence of the respective donor or cofactor thereof.

Multi-Compartment Kits

Disclosed herein is a multi-component coloring agent or kit comprising at least one first component comprising a direct dye composition (A) and a second component comprising a composition (B) containing, in a cosmetically acceptable aqueous medium:
  a) at least one photoprotective agent,
  b) at least one aromatic alcohol, and
  c) at least one carboxylic acid or a salt thereof.

A subject of the present disclosure is also a multi-component coloring agent or kit comprising at least one first component comprising a composition (A1) comprising at least one direct dye, a second component comprising a composition (A2) comprising at least one oxidizing agent, and a third component comprising a composition (B) containing, in a cosmetically acceptable aqueous medium:
  a) at least one photoprotective agent,
  b) at least one aromatic alcohol, and
  c) at least one carboxylic acid or a salt thereof.

A subject of the present disclosure is also a multi-component coloring agent or kit comprising at least one first component comprising a composition (A1) containing at least one oxidation dye precursor, a second component comprising a composition (A2) containing at least one oxidizing agent, and a third component comprising a composition (B) containing, in a physiologically and in particular cosmetically acceptable aqueous medium:
  a) at least one photoprotective agent,
  b) at least one aromatic alcohol, and
  c) at least one carboxylic acid or a salt thereof.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, unless otherwise indicated the numerical values set forth in the specific examples are reported as precisely as possible. Any numerical value, however, inherently contain certain errors necessarily resulting from the standard deviation found in their respective testing measurements.

In the text hereinbelow and hereinabove, the percentages are expressed on a weight basis.

By way of non-limiting illustration, concrete examples of certain embodiments of the present disclosure are given below. In the examples, AM means active material.

EXAMPLE

Permanent-waved hair was dyed blue using a dye composition described in Table 1 below, comprising an oxidation dyeing base: para-phenylenediamine, in equimolar combination with an oxidation dyeing coupler: 2,4-diaminophenoxyethanol.

TABLE 1

| Dye composition | Amounts |
| --- | --- |
| Hydroxyethylcellulose | 0.768 g % |
| Decyl glucoside | 5.4 g % |
| PEG-1412 | 2.7 g % |
| Benzyl alcohol | 1.8 g % |
| Ethanol | 18 g % |
| para-Phenylenediamine | $7.5 \times 10^{-4}$ mol % |
| 2,4-Diaminophenoxyethanol | $7.5 \times 10^{-4}$ mol % |
| Dissolvine | 1.08 g % |
| Sodium metabisulfite | 0.205 g % |
| Aqueous ammonia containing 20% ammonia | 10 g % |
| Demineralized water | qs 100 g % |

At the time of use, the above oxidation dye composition was mixed weight for weight with aqueous hydrogen peroxide solution (L'Oréal Professional 20-volumes aqueous hydrogen peroxide solution, containing 6% hydrogen peroxide).

The mixture was then applied to locks of permanent-waved hair, at a rate of 10 g of dye mixture/g of lock. The leave-in time was 15 minutes on each side of the lock.

The coloration was then stopped by rinsing with water followed by washing with a commercial shampoo (DOP camomile shampoo). The locks were then dried for 30 minutes at 60° C. under a drying hood.

Photoprotective Post-Treatments

The compositions described in Table 2 were then applied to the dyed locks, 24 hours after the dyeing operation described above.

TABLE 2

| Ingredients | Composition 1 (present disclosure) | Composition 2 (comparative) |
| --- | --- | --- |
| Ethanol | 15 g % | 15 g % |
| Benzyl alcohol | 5 g % | 5 g % |
| Benzoic acid | 0.2 g % | — |
| Citric acid | — | 0.2 g % |
| Benzophenone-4, sold under the name Uvinul MS40 by BASF | 20 g % AM | 20 g % AM |
| Demineralized water | qs 100 | qs 100 |
| Appearance | clear | Clear |

To do this, the dyed locks were treated with the above compositions. The contact time was 10 minutes at a temperature of 45° C.

The treatment was followed by elimination shampooing with a commercial shampoo (DOP camomile shampoo). The locks were then dried for 30 minutes at 60° C. under a drying hood.

UV Exposure

The dyed and treated locks were then exposed to UV over half their length for a period of 40 hours by means of a solar simulator, Xenotest 150S. The other half of the lock was masked with a piece of card paper.

The Xenotest 150S reproduces a reproducible light spectrum similar to that of sunlight via emission from an XE 1501 xenon arc lamp filtered with six infrared filters and a UV filter (UG11-black). The locks in rotation facing this radiation thus received an energy of 1250 W/m² in a spectral range from 300 to 800 nm (UV+visible) under conditions of 30° C. temperature and 51.6% relative humidity.

Evaluation of the Photoprotection

The degradation of the color after UV exposure was evaluated calorimetrically between the regions of masked and non-masked locks.

The measurements were taken using a Minolta CM 2022 spectrocolorimeter 24 hours after dyeing and 24 hours after the 40 hours of UV exposure.

The degradation caused by the UV is expressed in $\Delta E$ $$\Delta E^2 = (\Delta L^*_{after\ exposure} - \Delta L^*_{before\ exposure})^2 + (\Delta a^*_{after\ exposure} - \Delta a^*_{before\ exposure})^2 + (\Delta b^*_{after\ exposure} - \Delta b^*_{before\ exposure})^2$$

The results obtained are indicated in Table 3 below:

TABLE 3

| Composition | $\Delta E$ |
| --- | --- |
| Untreated control | 11.47 |
| Composition 1 (present disclosure) | 5.07 |
| Composition 2 (comparative) | 7.6 |

It was observed that composition 1 according to the present disclosure containing benzoic acid showed better light-fastness of the color of the hair after 40 hours of UV exposure, compared with that obtained with composition 2 not containing benzoic acid.

What is claimed is:

1. A hair-care product comprising, in a physiologically acceptable aqueous medium:
    (a) at least one agent for protecting artificially dyed human hair, chosen from organic UV-screening agents, and present in an amount ranging from 0.2% to 20% by weight relative to the total weight of the composition;

(b) at least one aromatic alcohol comprising at least one benzene ring and at least one alcohol (OH) function directly linked to at least one substituent of said ring, wherein said at least one aromatic alcohol is present in an amount ranging from greater than 1% to 5% by weight relative to the total weight of the composition; and (c) at least one aromatic carboxylic acid chosen from benzene rings having at least one carboxylic acid function directly linked to the ring or a salt thereof, present in an amount ranging from about 0.1% to about 10% by weight relative to the total weight of the composition.

2. The composition of claim 1, wherein the aqueous medium comprises water and at least one organic solvent other than aromatic alcohols and aromatic carboxylic acids.

3. The composition of claim 2, wherein the at least one organic solvent is chosen from $C_1$-$C_4$ lower alcohols and polyols.

4. The composition of claim 3, wherein the at least one organic solvent is ethanol.

5. The composition of claim 1, wherein the organic UV-screening agents are chosen from water-soluble or liposoluble, silicone, or non-silicone screening agents.

6. The composition of claim 5, wherein the organic UV-screening agents are chosen from dibenzoylmethane derivatives; anthranilates; cinnamic derivatives; salicylic derivatives; benzylidenecamphor derivatives; benzophenone derivatives; β,β-diphenylacrylate derivatives; triazine derivatives; phenylbenzotriazole derivatives; benzalmalonate derivatives; phenylbenzimidazole derivatives; imidazolines; bis-benzazolyl derivatives; p-aminobenzoic acid (PABA) derivatives; benzoxazole derivatives; screening polymers and screening silicones; α-alkylstyrene-based dimers; 4,4-diarylbutadienes, and mixtures thereof.

7. The composition of claim 6, wherein the liposoluble organic UV-screening agents are chosen from:
butyl methoxydibenzoylmethane,
ethyl hexyl methoxycinnamate,
Homosalate,
ethyl hexyl salicylate,
Octocrylene,
Benzophenone-3,
n-hexyl 2-(4-diethylamino-2-hydroxybenzoyl)benzoate,
4-methylbenzylidenecamphor,
ethyl hexyl triazone,
bis-ethylhexyloxyphenol methoxyphenyl triazine,
diethylhexyl butamido triazone,
drometrizole trisiloxane,
Polysilicone-15,
1,1-dicarboxy(2,2'-dimethylpropyl)-4,4-diphenylbutadiene,
2,4-bis[5-1(dimethylpropyl)benzoxazol-2-yl(4-phenyl)imino]-6-(2-ethylhexyl)imino-1,3,5-triazine, and
mixtures thereof.

8. The composition of claim 5, wherein the water-soluble organic UV-screening agents are chosen from:
PABA,
PEG-25 PABA,
benzylidenecamphorsulfonic acid,
camphorbenzalkonium methosulfate,
terephthalylidenedicamphorsulfonic acid,
phenylbenzimidazolesulfonic acid,
disodium phenylbenzimidazoletetrasulfonate,
Benzophenone-4, and
Benzophenone-5.

9. The composition of claim 1, wherein the at least one protecting agent is soluble in the aqueous medium of the composition.

10. The composition of claim 9, wherein the at least one protecting agent has a log P (octanol/water partition coefficient) of less than 9.

11. The composition of claim 10, wherein the at least one protecting agent has a log P of less than 4.

12. The composition of claim 9, wherein the at least one protecting agent is soluble to at least 0.5% in water and $C_1$-$C_4$ lower alcohols at 25° C.

13. The composition of claim 1, wherein the at least one protecting agent is a water-soluble organic UV-screening agent.

14. The composition of claim 13, wherein the water-soluble UV-screening agent is Benzophenone-4.

15. The composition of claim 1, wherein the at least one aromatic alcohol is chosen from:
benzyl alcohol,
benzoylisopropanol,
benzyl glycol,
phenoxyethanol,
dichlorobenzyl alcohol,
methylphenylbutanol,
phenoxyisopropanol,
phenylisohexanol,
phenylpropanol,
phenylethyl alcohol, and
mixtures thereof.

16. The composition of claim 15, wherein the at least one aromatic alcohol is benzyl alcohol.

17. The composition of claim 1, wherein the at least one aromatic carboxylic acid is chosen from:
benzoic acid,
para-anisic acid,
caffeic acid,
chlorogenic acid,
diphenolic acid,
ferulic acid,
hippuric acid,
3-hydroxybenzoic acid,
4-hydroxybenzoic acid,
hydroxycinnamic acid,
phenylthioglycolic acid,
salicylic acid,
acetylsalicylic acid,
para-, meta-, and ortho-phthalic acid,
the salified forms thereof, and
mixtures thereof.

18. The composition of claim 17, wherein the at least one aromatic carboxylic acid is benzoic acid.

19. The composition of claim 1, further comprising at least one conditioning agent.

20. The composition of claim 19, wherein the at least one conditioning agent is present in the composition in an amount ranging from 0.001% to 20% by weight relative to the total weight of the composition.

21. The composition of claim 20, wherein the at least one conditioning agent is present in the composition in an amount ranging from 0.01% to 10% by weight relative to the total weight of the composition.

22. The composition of claim 21, wherein the at least one conditioning agent is present in the composition in an amount ranging from 0.1% to 3% by weight relative to the total weight of the composition.

23. The composition of claim 1, further comprising at least one surfactant chosen from anionic, cationic, amphoteric, and nonionic surfactants.

24. The composition of claim 23, wherein the at least one surfactant is present in the composition in an amount ranging from 0.1% to 60% by weight relative to the total weight of the composition.

25. The composition of claim 24, wherein the at least one surfactant is present in the composition in an amount ranging from 1% to 40% by weight relative to the total weight of the composition.

26. The composition of claim 25, wherein the at least one surfactant is present in the composition in an amount ranging from 5% to 30% by weight relative to the total weight of the composition.

27. The composition of claim 1, wherein the composition is in the form of a shampoo and further comprises a washing base.

28. The composition of claim 27, wherein at least one surfactant forms the washing base and is present in the composition in an amount ranging from 4% to 50% by weight relative to the total weight of the composition.

29. The composition of claim 28, wherein the at least one surfactant forming the washing base is present in the composition in an amount ranging from 6% to 35% by weight relative to the total weight of the composition.

30. The composition of claim 29, wherein the at least one surfactant forming the washing base is present in the composition in an amount ranging from 8% to 25% by weight relative to the total weight of the composition.

31. The composition of claim 30, wherein the at least one surfactant forming the washing base is chosen from anionic surfactants and present in the composition in an amount of at least 3% by weight relative to the total weight of the composition.

32. The composition of claim 31, wherein the at least one surfactant forming the washing base is present in the composition in an amount ranging from 4% to 30% by weight relative to the total weight of the composition.

33. The composition of claim 1, wherein the composition is in the form of an aqueous or aqueous-alcoholic lotion, a gel, a milk, a cream, an emulsion, or a mousse.

34. The composition of claim 1, wherein the composition is packaged in a vaporizer, a pump-dispenser bottle, or in an aerosol container.

35. The composition of claim 1, wherein the composition is in the form of a rinse-out or leave-in hair conditioner or in the form of a composition to be applied to artificially dyed human hair after dyeing, bleaching, permanent-waving and/or relaxing the keratin fibers or between the two steps of a permanent-waving or hair-relaxing operation.

36. The composition of claim 1, wherein the pH of the composition ranges from 1 to 11.

37. The composition of claim 36, wherein the pH ranges from 2 to 6.

38. A method for protecting artificially dyed human hair against the action of atmospheric agents comprising applying to the artificially dyed human hair a hair-care product comprising, in a physiologically acceptable aqueous medium:
(a) at least one agent for protecting artificially dyed human hair, chosen from organic UV-screening agents, present in an amount ranging from 0.2% to 20% by weight relative to the total weight of the composition;
(b) at least one aromatic alcohol comprising at least one benzene ring and at least one alcohol (OH) function directly linked to at least one substituent of said ring, wherein said at least one aromatic alcohol is present in an amount ranging from greater than 1% to 5% by weight relative to the total weight of the composition; and
(c) at least one aromatic carboxylic acid chosen from benzene rings haying at least one carboxylic acid function directly linked to the ring or a salt thereof, present in an amount ranging from about 0.1% to about 10% by weight relative to the total weight of the composition.

39. A method for the post-treatment of artificially dyed human hair comprising applying to artificially dyed human hair a hair-care product comprising, in a physiologically acceptable aqueous medium:
(a) at least one agent for protecting artificially dyed human hair, chosen from organic UV-screening agents, present in an amount ranging from 0.2% to 20% by weight relative to the total weight of the composition;
(b) at least one aromatic alcohol comprising at least one benzene ring and at least one alcohol (OH) function directly linked to at least one substituent of said ring, wherein said at least one aromatic alcohol is present in an amount ranging from greater than 1% to 5% by weight relative to the total weight of the composition; and
(c) at least one aromatic carboxylic acid chosen from benzene rings haying at least one carboxylic acid function directly linked to the ring or a salt thereof, present in an amount ranging from about 0.1% to about 10% by weight relative to the total weight of the composition.

40. The method of claim 39, wherein the artificially dyed human hair is dyed by direct dyeing or by oxidation dyeing.

41. A method for dyeing keratin fibers comprising:
(A) applying to the keratin fibers a direct or oxidation dye composition (A) for a time that is sufficient to develop color, and, after optionally rinsing and optionally drying,
(B) applying to the keratin fibers a composition (B) comprising a hair-care product either immediately or in a delayed manner, and
(C) optionally repeating (A) and (B),
wherein the hair-care product comprises, in a physiologically acceptable aqueous medium:
(a) at least one agent for protecting artificially dyed human hair, chosen from organic UV-screening agents, present in an amount ranging from 0.2% to 20% by weight relative to the total weight of the composition;
(b) at least one aromatic alcohol comprising at least one benzene ring and at least one alcohol (OH) function directly linked to at least one substituent of said ring, wherein said at least one aromatic alcohol is present in an amount ranging from greater than 1% to 5% by weight relative to the total weight of the composition; and
(c) at least one aromatic carboxylic acid chosen from benzene rings haying at least one carboxylic acid function directly linked to the ring or a salt thereof, present in an amount ranging from about 0.1% to about 10% by weight relative to the total weight of the composition.

42. A multi-component coloring agent comprising at least one first component comprising a direct or oxidation dye composition (A) and a second component comprising a post-treatment composition (B) comprising, in a physiologically acceptable aqueous medium:
(a) at least one agent for protecting artificially dyed human hair, chosen from organic UV-screening agents, present in an amount ranging from 0.2% to 20% by weight relative to the total weight of the composition;

(b) at least one aromatic alcohol comprising at least one benzene ring and at least one alcohol (OH) function directly linked to at least one substituent of said ring, wherein said at least one aromatic alcohol is present in an amount ranging from greater than 1% to 5% by weight relative to the total weight of the composition; and (c) at least one aromatic carboxylic acid chosen from benzene rings haying at least one carboxylic acid function directly linked to the ring or a salt thereof, present in an amount ranging from about 0.1% to about 10% by weight relative to the total weight of the composition.

43. A multi-component coloring agent comprising at least one first component comprising a composition (A1) comprising at least one direct dye, a second component comprising a composition (A2) comprising at least one oxidizing agent, and a third component comprising a post-treatment composition (B) comprising, in a physiologically acceptable aqueous medium:

(a) at least one agent for protecting artificially dyed human hair, chosen from organic UV-screening agents, present in an amount ranging from 0.2% to 20% by weight relative to the total weight of the composition;

(b) at least one aromatic alcohol comprising at least one benzene ring and at least one alcohol (OH) function directly linked to at least one substituent of said ring, wherein said at least one aromatic alcohol is present in an amount ranging from greater than 1% to 5% by weight relative to the total weight of the composition; and (c) at least one aromatic carboxylic acid chosen from benzene rings having at least one carboxylic acid function directly linked to the ring or a salt thereof, present in an amount ranging from about 0.1% to about 10% by weight relative to the total weight of the composition.

44. A multi-component coloring agent comprising at least one first component comprising a composition (A1) comprising at least one oxidation dye precursor, a second component comprising a composition (A2) comprising at least one oxidizing agent, and a third component comprising a post-treatment composition (B) comprising, in a physiologically acceptable aqueous medium:

(a) at least one agent for protecting artificially dyed human hair, chosen from organic UV-screening agents, present in an amount ranging from 0.2% to 20% by weight relative to the total weight of the composition;

(b) at least one aromatic alcohol comprising at least one benzene ring and at least one alcohol (OH) function directly linked to at least one substituent of said ring, wherein said at least one aromatic alcohol is present in an amount ranging from greater than 1% to 5% by weight relative to the total weight of the composition; and (c) at least one aromatic carboxylic acid chosen from benzene rings having at least one carboxylic acid function directly linked to the ring or a salt thereof, present in an amount ranging from about 0.1% to about 10% by weight relative to the total weight of the composition.

* * * * *

UNITED STATES PATENT AND TRADEMARK OFFICE
CERTIFICATE OF CORRECTION

PATENT NO. : 8,790,623 B2
APPLICATION NO. : 11/333292
DATED : July 29, 2014
INVENTOR(S) : Boris Lalleman et al.

It is certified that error appears in the above-identified patent and that said Letters Patent is hereby corrected as shown below:

Title page, Column 1, item (73) Assignee: "Il'Oreal" should be -- L'Oreal --.

Signed and Sealed this
Seventh Day of October, 2014

Michelle K. Lee
*Deputy Director of the United States Patent and Trademark Office*